US012758307B2

(12) United States Patent
Sheth et al.

(10) Patent No.: US 12,758,307 B2

(45) Date of Patent: Oct. 13, 2026

(54) CATHETER DEFLECTION CONTROL ASSEMBLY

(71) Applicant: Biosense Webster (Israel) Ltd., Yokneam (IL)

(72) Inventors: Piyush K. Sheth, Porter Ranch, CA (US); Jeffrey L. Clark, Maineville, OH (US)

(73) Assignee: Biosense Webster (Israel) Ltd., Yokneam (IL)

( * ) Notice: Subject to any disclaimer, the term of this patent is extended or adjusted under 35 U.S.C. 154(b) by 485 days.

(21) Appl. No.: 17/089,772

(22) Filed: Nov. 5, 2020

(65) Prior Publication Data

US 2021/0177506 A1 Jun. 17, 2021

Related U.S. Application Data

(60) Provisional application No. 62/948,527, filed on Dec. 16, 2019.

(51) Int. Cl.

*A61B 18/14* (2006.01)
*A61B 18/00* (2006.01)
*A61M 25/01* (2006.01)

(52) U.S. Cl.

CPC *A61B 18/1492* (2013.01); *A61B 2018/00351* (2013.01); *A61B 2018/00577* (2013.01);

(Continued)

(58) Field of Classification Search

CPC ...... A61B 18/1492; A61B 2018/00351; A61B 2018/00916; A61B 2018/00577;

(Continued)

(56) References Cited

U.S. PATENT DOCUMENTS 4,534,339 A * 8/1985 Collins .............. A61B 1/00128 600/146
5,364,351 A * 11/1994 Heinzelman ...... A61M 25/0147 604/95.04

(Continued)

FOREIGN PATENT DOCUMENTS

EP 1803481 A2 7/2007
WO WO 2007/002713 A2 1/2007

(Continued)

OTHER PUBLICATIONS

U.S. Appl. No. 62/866,109, filed Jun. 25, 2019, by Hoitink, et al., entitled: "Catheter Deflection System With Deflection Load Limiter."

(Continued)

*Primary Examiner* — Beverly M Flanagan
*Assistant Examiner* — Abigail M Ziegler
(74) *Attorney, Agent, or Firm* — FBT Gibbons LLP

(57) ABSTRACT

An apparatus includes a handle, a catheter, an end effector, and a deflection drive assembly. The end effector includes at least one electrode. The deflection drive assembly includes an input member, a translating assembly coupled to the end effector, and a rack and pinion assembly. The rack and pinion assembly is configured to drive the translating assembly to deflect the end effector away at an angle relative to the longitudinal axis and consists of a rack and a pinion. The rack and pinion assembly is configured to either transfer rotational motion of the pinion from the input member into linear motion of the rack to push distally or pull proximally the translating member; or transfer linear motion of the rack from the input member into rotational motion of the pinion to move a first end of the translating member proximally and a second end of the translating member distally.

20 Claims, 19 Drawing Sheets

(52) U.S. Cl.
CPC ................. *A61B 2018/0091* (2013.01); *A61B 2018/00916* (2013.01); *A61M 25/0133* (2013.01); *A61M 25/0136* (2013.01); *A61M 25/0147* (2013.01)

(58) Field of Classification Search
CPC .. A61B 2018/00839; A61B 2018/0091; A61B 2017/00323; A61M 25/0136; A61M 25/0147; A61M 25/0133
See application file for complete search history.

(56) References Cited

U.S. PATENT DOCUMENTS

| | | | | |
|---|---|---|---|---|
| 6,171,277 | B1 | 1/2001 | Ponzi | |
| 6,913,594 | B2 | 7/2005 | Coleman et al. | |
| 7,465,288 | B2 * | 12/2008 | Dudney | A61M 25/0136 604/95.04 |
| 8,066,167 | B2 | 11/2011 | Measamer et al. | |
| 9,480,416 | B2 | 11/2016 | Govari et al. | |
| 9,801,585 | B2 | 10/2017 | Shah et al. | |
| 10,130,422 | B2 | 11/2018 | Ditter | |
| 10,569,053 | B2 | 2/2020 | Gonzalez | |
| 10,660,700 | B2 | 5/2020 | Beeckler et al. | |
| 10,702,177 | B2 | 7/2020 | Aujla | |
| 10,743,932 | B2 | 8/2020 | Gallardo et al. | |
| 2005/0096590 | A1 | 5/2005 | Gullickson et al. | |
| 2005/0277874 | A1 | 12/2005 | Selkee | |
| 2007/0016164 | A1 | 1/2007 | Dudney et al. | |
| 2007/0156116 | A1 * | 7/2007 | Gonzalez | A61M 25/0136 604/528 |
| 2007/0179340 | A1 | 8/2007 | Jorgensen | |
| 2009/0112229 | A1 | 4/2009 | Omori et al. | |
| 2009/0157060 | A1 * | 6/2009 | Teague | A61B 17/00234 606/1 |
| 2010/0168756 | A1 | 7/2010 | Dorn et al. | |
| 2012/0083836 | A1 * | 4/2012 | Shelton, IV | A61B 17/0644 206/339 |
| 2014/0088497 | A1 * | 3/2014 | Campbell | A61M 25/0136 604/95.04 |
| 2014/0128889 | A1 * | 5/2014 | Sullivan | A61B 17/0483 606/144 |
| 2014/0324015 | A1 | 10/2014 | Romoscanu | |
| 2014/0330251 | A1 | 11/2014 | Romoscanu | |
| 2014/0364802 | A1 * | 12/2014 | Schneider | A61M 25/0136 604/95.04 |
| 2015/0374365 | A1 | 12/2015 | Schuckmann et al. | |
| 2016/0206853 | A1 | 7/2016 | Bolduc et al. | |

FOREIGN PATENT DOCUMENTS

| | | | |
|---|---|---|---|
| WO | WO 2009/057347 | A1 | 5/2009 |
| WO | 2017/043128 | A1 | 3/2017 |
| WO | WO 2017/106235 | A1 | 6/2017 |

OTHER PUBLICATIONS

U.S. Appl. No. 62/948,527, filed Dec. 16, 2019, by Sheth, et al., entitled: "Catheter Deflection Control Assembly."
International Search Report and Written Opinion dated Mar. 29, 2021, for International Application No. PCT/US2020/070885, 14 pages.
International Preliminary Report on Patentability issued May 17, 2022, in corresponding PCT Application No. PCT/US2020/070885, 11 pages.
Japanese Office Action, Notification of Reasons for Refusal, dated May 28, 2024 for Application No. JP 2022-536784, 6 pgs.
Japanese Office Action, Final, dated Nov. 12, 2024 for Application No. JP 2022-536784, 2 pgs.
Chinese First Office Action and Search Report dated Jun. 3, 2025, for Application No. 202080087345.9, 9 pages.
Chinese Second Office Action and Supplemental Search Report dated Jan. 21, 2026, for Application No. 202080087345.9, 8 pages.
Notice Of Allowance, received for Chinese Patent Application No. 202080087345.9, mailed on May 28, 2026, 7 pages (2 pages of English translation and 5 pages of original document).

* cited by examiner

CATHETER DEFLECTION CONTROL ASSEMBLY

PRIORITY

This application claims priority to U.S. Provisional Pat. App. No. 62/948,527, entitled "Catheter Deflection Control Assembly," filed Dec. 16, 2019, the disclosure of which is incorporated by reference herein, in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of EP mapping systems and catheters are described in various references cited herein.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. OVERVIEW OF EXEMPLARY ABLATION CATHETER SYSTEM

Figure 1:
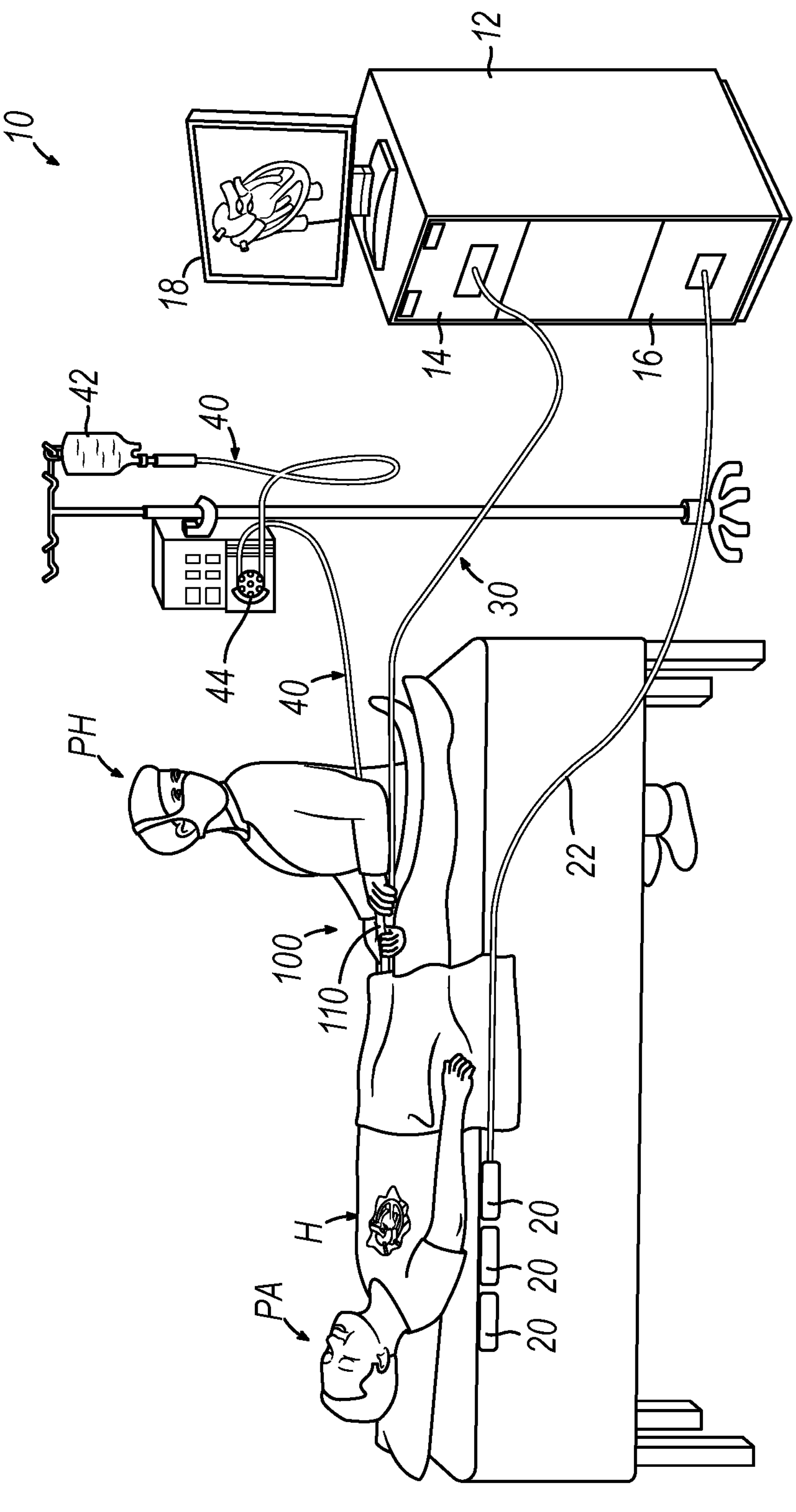
FIG. 1 depicts a schematic perspective view of a medical procedure in which a catheter of a catheter assembly is inserted in a patient.
Figure 2:
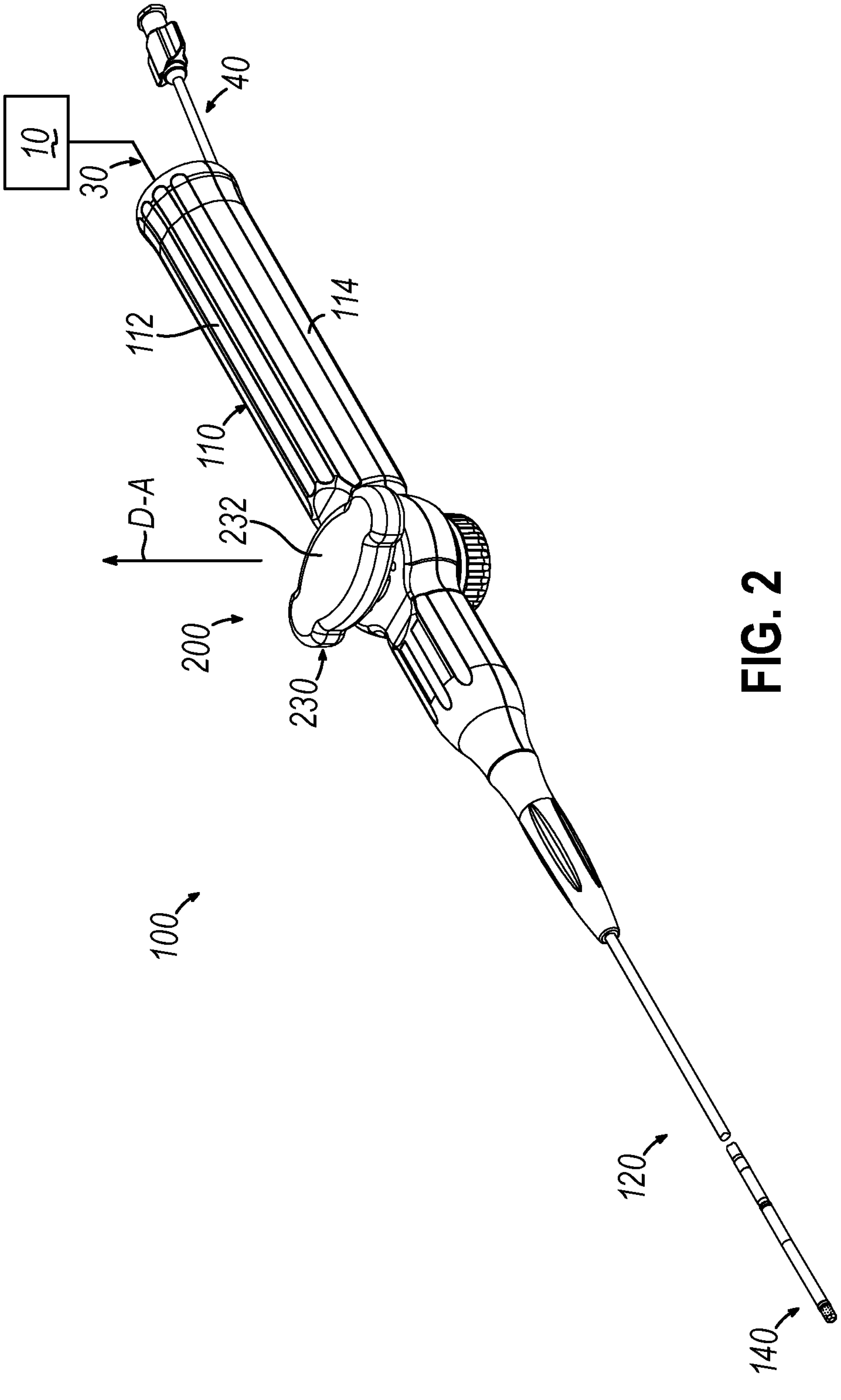
FIG. 2 depicts a perspective view of the catheter assembly of FIG. 1, with additional components shown in schematic form.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2-3 but not shown in FIG. 1) of catheter assembly (100) disposed in a patient (PA) to ablate tissue in or near the heart (H) of the patient (PA). As shown in FIG. 2, catheter assembly (100) includes handle (110), catheter (120) extending distally from handle (110), end effector (140) located at a distal end of catheter (120), and a deflection drive assembly (200) associated with handle (110).

As will be described in greater detail below, end effector (140) includes various components configured to deliver RF energy to targeted tissue sites, provide EP mapping functionality, track external forces imparted on end effector (140), track the location of end effector (140), and disperse irrigation fluid. As will also be described in greater detail below, deflection drive assembly (200) is configured to deflect end effector (140) and a distal portion of catheter (120) away from a central longitudinal axis (L-L) (FIGS. 3-5) defined by a proximal portion of catheter (120).

Figure 3:
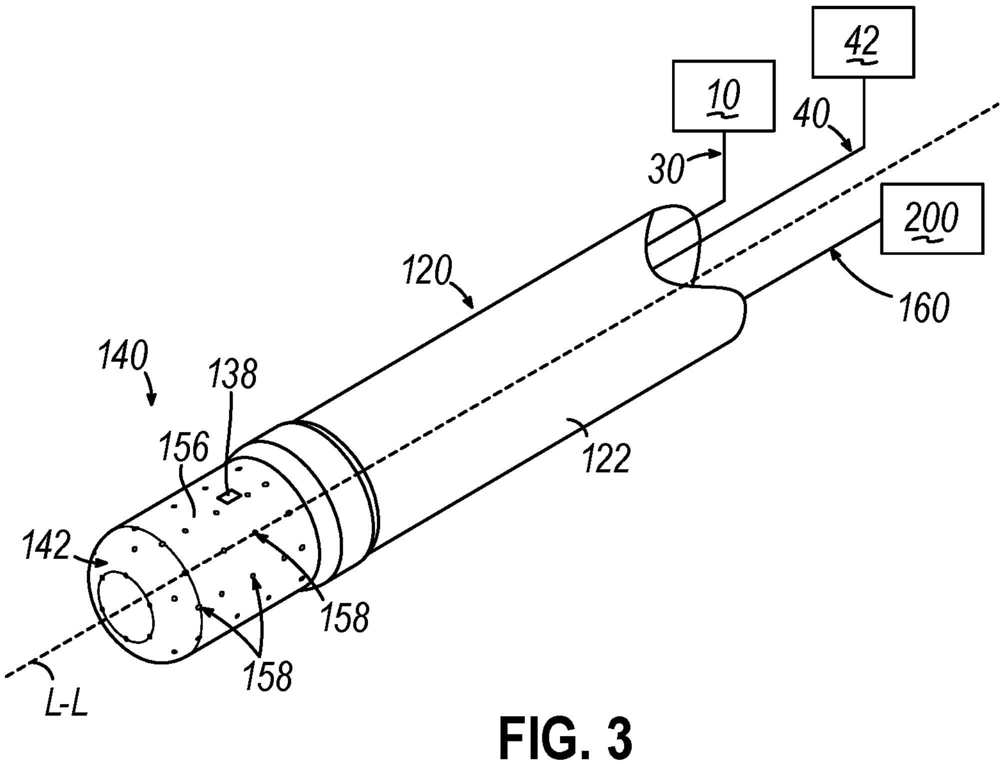
FIG. 3 depicts a perspective view of a distal portion of the catheter of FIG. 1, with additional components shown in schematic form.

As shown in FIG. 3, catheter (120) includes an elongate flexible sheath (122), with end effector (140) being disposed at a distal end of outer sheath (122). End effector (140) and various components that are contained in outer sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H). First driver module (14) is also operable to receive position indicative signals from a navigation sensor assembly (150) in end effector (140). In such versions, the processor of console (12) is also operable to process the position indicative signals from navigation sensor assembly (150) to thereby determine the position of end effector (140) within the patient (PA).

Navigation sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a navigation sensor assembly (150).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from navigation sensor assembly (150) of end effector (140). For instance, as end effector (140) of catheter (120) moves within the patient (PA), the corresponding position data from navigation sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (140) on the images of the patient's anatomy, such as by superimposing an illuminated dot, a crosshair, a graphical representation of end effector (140), or some other form of visual indication. Such a superimposed visual indication may also move within the images of the patient anatomy on display (18) in real time as the physician (PH) moves end effector (140) within the patient (PA), thereby providing real-time visual feedback to the operator about the position of end effector (140) within the patient (PA) as end effector (140) moves within the patient (PA). The images provided through display (18) may thus effectively provide a video tracking of the position of end effector (140) within a patient (PA), without necessarily having any optical instrumentation (i.e., cameras) viewing end effector (140). In the same view, display (18) may simultaneously visually indicate the locations of aberrant conductive tissue sites detected through EP mapping. The physician (PH) may thus view display (18) to observe the real time positioning of end effector (140) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. EXEMPLARY END EFFECTOR OF CATHETER ASSEMBLY

Figure 4:
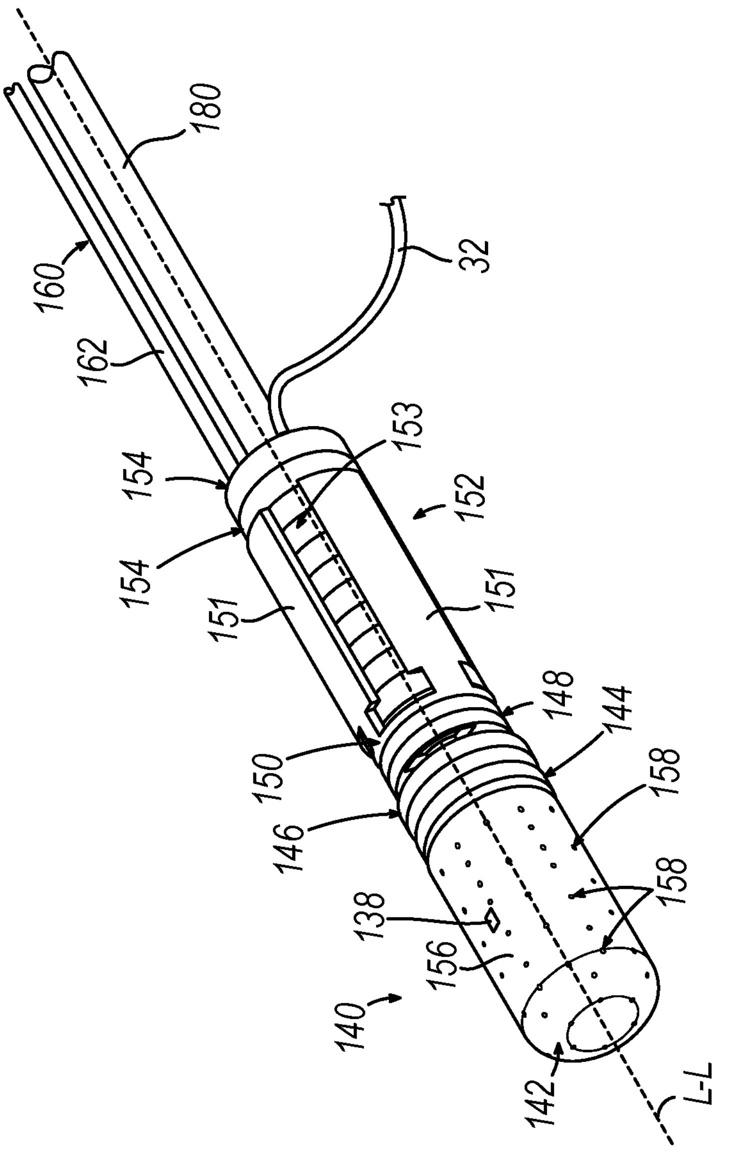
FIG. 4 depicts a perspective view of the distal portion of the catheter of FIG. 1, with an outer sheath omitted to reveal internal components.
Figure 5:
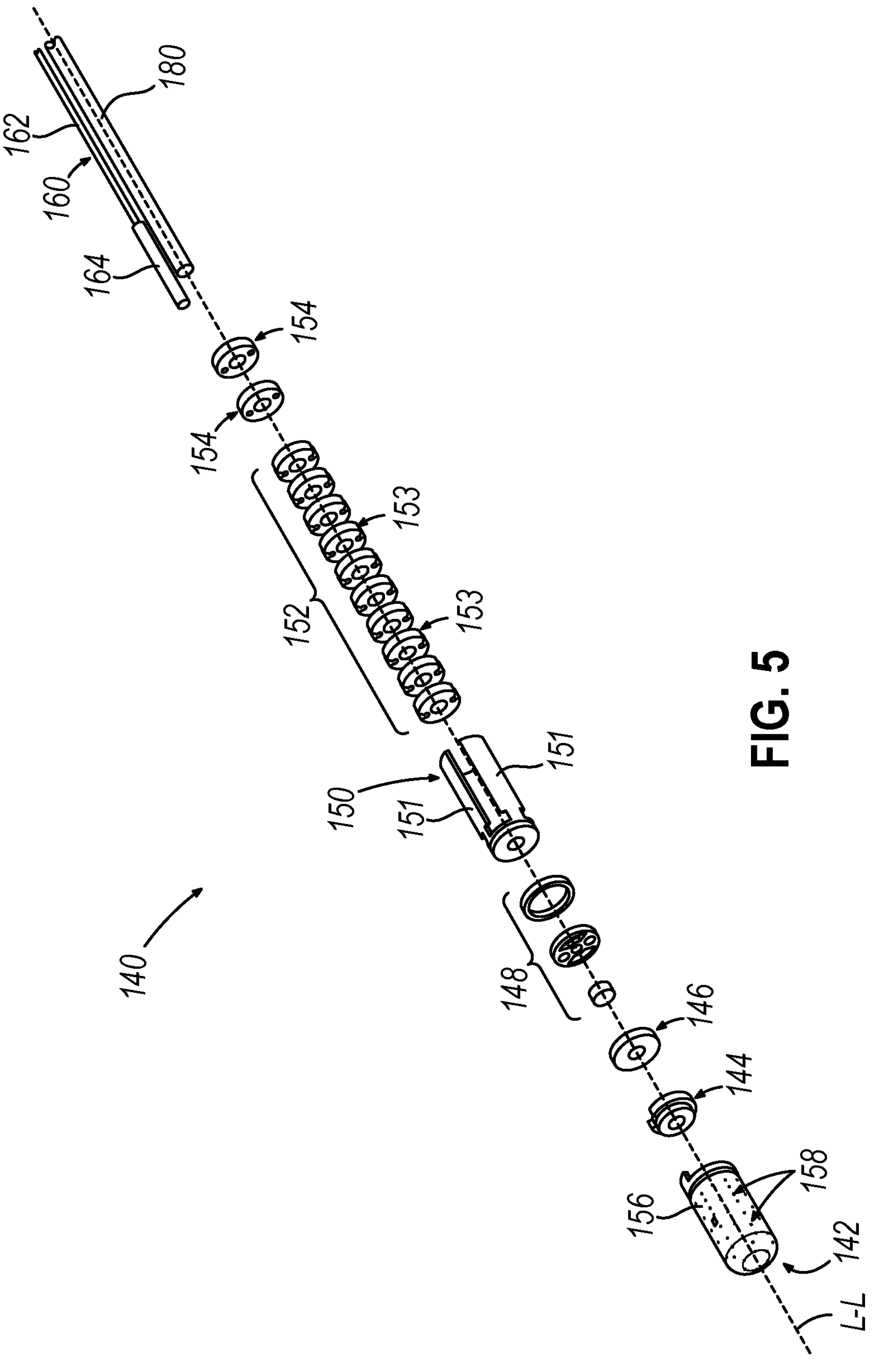
FIG. 5 depicts an exploded perspective view of the distal portion of the catheter of FIG. 1.

FIGS. 3-5 show exemplary components of end effector (140), and other components of the distal portion of catheter (120), in greater detail. As mentioned above, end effector (140) includes various components configured to deliver RF energy to targeted tissue sites, provide EP mapping functionality, track external forces imparted on end effector (140), track the location of end effector (140) within the patient (PA), and disperse irrigation fluid. For example, end effector (140) includes distal tip member (142), a distal tip base (144), a distal circuit disk (146), a strain gauge assembly (148), a navigation sensor assembly (150), a distal spacer stack (152), and a pair of proximal spacers (154). Distal tip member (142), distal tip base (144), distal circuit disk (146), strain gauge assembly (148), navigation sensor assembly (150), distal spacer stack (152), and proximal spacers (154) are coaxially aligned with each other and are stacked longitudinally so that these components (144-154) define a stacked circuit. Push-pull cable (160) and an irrigation tube (180) may extend along the length of catheter (120) to reach end effector (140). Each of the foregoing components will be described in greater detail below. Outer sheath (122), which may be flexible, surrounds all of the foregoing components except for distal tip member (142).

As shown in FIGS. 3-5, distal tip member (142) of the present example includes a cylindraceous body (156) with a dome tip. Cylindraceous body (156) and the dome tip may be formed of an electrically conductive material, such as metal. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximal-most spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). EP mapping microelectrodes (138) may thus be used to determine locations of aberrant electrical activity in tissue within a cardiovascular anatomical structure (e.g., pulmonary vein, etc.). Signals picked up by EP mapping microelectrodes (138) may be communicated through vias or other structures in the layers that are proximal to strain gauge assembly (148), eventually reaching first driver module (14) of console (12) via cable (30). First driver module (14) may process the EP mapping signals and provide the physician (PH) with corresponding feedback indicating the locations of aberrant electrical activity in accordance with the teachings of various references cited herein.

In versions where cylindraceous body (156) is formed of an electrically conductive material to provide RF electrical energy for tissue ablation, an electrically insulating material may be interposed between cylindraceous body (156) and EP mapping microelectrodes (138) to thereby electrically isolate EP mapping microelectrodes (138) from cylindraceous body (156). EP mapping microelectrodes (138) may be constructed and operable in accordance with the teachings of various patent references cited herein. While only one EP mapping microelectrode (138) is shown, distal tip member (142) may include two or more EP mapping microelectrodes (138). Alternatively, distal tip member (142) may lack EP mapping microelectrodes (138) altogether. Distal tip base (144) defines a central aperture configured to provide a path for communication of irrigation fluid to the hollow interior of distal tip member (142). Distal tip base (144) forms an annular shoulder that the proximal edge of distal tip member (142) may abut. Distal tip member (142) also defines a lateral notch that is configured to receive a proximally extending tab of distal tip member (142).

As shown in FIGS. 3-4, distal circuit disk (146) is positioned proximal to distal tip base (144). Distal circuit disk (146) includes circuitry that is operable to communicate RF electrical energy to distal tip member (142) via the proximally extending tab of distal tip member (142). In versions where one or more EP mapping electrodes (138) are included, distal circuit disk (146) may also include circuitry that is operable to communicate EP mapping signals from EP mapping electrodes (138). In some versions, distal circuit disk (146) further includes one or more transmission coils. Such transmission coils may provide wireless communication of signals (e.g., EP mapping signals from microelectrodes (138)) to one or more complementary coils that are proximal to distal circuit disk (146). In addition, or in the alternative, such transmission coils may provide wireless communication of RF electrical energy from one or more complementary coils that are proximal to distal circuit disk (146) to distal tip member (142).

In versions where coils are incorporated into distal circuit disk (146) and one or more other layers that are proximal to strain gauge assembly (148), such coils may thus enable wireless communication of electrical signals across strain gauge assembly (148) without requiring wires, vias, or other electrically conductive structures to pass longitudinally across strain gauge assembly (148). In some versions, distal circuit disk (146) includes at least one transmission coil (TX) that is paired with receiving coil (RX) of navigation sensor assembly (150) to detect strain being applied to strain gauge assembly (148) so as to determine the contact force applied to distal tip member (142). Some other versions of distal circuit disk (146) may simply omit a TX coil.

Strain gauge assembly (148) is positioned proximal to distal circuit disk (146) and is configured to sense external forces that impinge against distal tip member (142). When distal tip (142) encounters external forces (e.g., when distal tip (142) is pressed against tissue), those external forces are communicated from distal tip (142) to distal tip base (144), to distal circuit disk (146), and to strain gauge assembly (148) such that strain gauge may generate a suitable signal corresponding to the magnitude and direction of the external force. The signals from strain gauge assembly (148) may be communicated through vias or other structures in the layers that are proximal to strain gauge assembly (148), eventually reaching first driver module (14) of console (12) via cable (30). First driver module (14) may process the strain signals in accordance with any suitable fashion as would be apparent to one of ordinary skill in the art in view of the teachings herein. By way of example only, console (12) may provide audible feedback to alert the physician (PH) when strain gauge assembly (148) indicates that distal tip member (142) is encountering forces over a predetermined threshold, to thereby prevent the physician (PH) from unwittingly damaging a cardiovascular anatomical structure with distal tip member (142).

Navigation sensor assembly (150) may generate signals indicating the position and orientation of end effector (140) in three-dimensional space with substantial precision. Navigation sensor assembly (150) includes a plurality of panels (151), each including an RX coil that is operable to generate position-indicative electrical signals in response to the alternating magnetic fields generated by field generators (20). Each RX coil may be formed by electrical traces to define an electrical coil or antenna to receive radiofrequency signals emitted by external transmitters TX coils (e.g., three TX coils provided by field generators (20) positioned external of the patient (PA) body and emitting discrete radiofrequencies) such that the location and orientation of each RX coil can be determined with respect to the TX coils provided by field generators (20). The signals from navigation sensor assembly (150) may be communicated through vias or other structures in the layers that are proximal to strain navigation sensor assembly (150), eventually reaching first driver module (14) of console (12) via cable (30).

A central annular body of navigation sensor assembly (150) defines a central aperture configured to provide a path for communication of irrigation fluid to the hollow interior of distal tip member (142). In versions where central annular body of navigation sensor assembly includes wireless communication coils, such wireless communication coils may be further coupled with vias or other structures in the layers that are proximal to strain navigation sensor assembly (150), thereby providing a path for electrical communication with first driver module (14) of console (12) via cable (30).

In the present example, each distal spacer (153) is generally shaped like a disk, with a pair of chordal cutouts angularly offset from each other by 90 degrees. These cutouts are sized and configured to accommodate a respective panel (151) of navigation sensor assembly (150), thereby allowing panels (151) to be radially interposed between distal spacer stack (152) and outer sheath (122). Each distal spacer (153) also includes at least one cable notch, where two or more notches may be angularly offset from each other by 180 degrees. This cable notch is configured to receive distal end portion (164) of push-pull cable (160). Each distal spacer (153) further includes a central aperture configured to provide a path for communication of irrigation fluid to the hollow interior of distal tip member (142). Each proximal spacer (154) is shaped like a disk, with two or more apertures formed therethrough. A central aperture is configured to provide a path for communication of irrigation fluid to the hollow interior of distal tip member (142). The side aperture is sized and configured to receive proximal portion (162) of push-pull cable (160). A second side aperture may also be included.

As noted above and as shown in FIGS. 1 and 3, cable (30) couples catheter assembly (100) with drive system (10). As shown in FIG. 4, wires (32) of cable (30) extend along the length of catheter (120) to reach the proximal-most proximal spacer (154). Wires (32) may thus be contained within outer sheath (122). Wires (32) may be physically and electrically coupled with the proximal-most proximal spacer (154) in any suitable fashion. Catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 4-5. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through the central passageway, ultimately reaching the interior of distal tip member (142) via aperture (218) of distal tip base (144).

As best shown in FIG. 5, respective distal end portion (164) has a larger outer diameter than the outer diameter of respective intermediary portions (162). Distal end portion (174) is coupled with end effector (140) to prevent push-pull cable (160) from being pulled proximally out of end effector (140). Suitable ways in which push-pull cable (160) may be coupled with end effector (140) will be apparent to those skilled in the art in view of the teachings herein.

III. EXEMPLARY CATHETER ASSEMBLIES WITH EXEMPLARY DEFLECTION DRIVE ASSEMBLIES

In some instances, multiple production lines are used for construction of catheters. For example, a first production line may produce only uni-directional catheters, and a second production line may produce only bi-directional catheters. A uni-directional catheter is a catheter that deflects in only a single direction (e.g. up, down, left, or right) away from longitudinal axis (L-L). A bi-directional catheter is a catheter that deflects in two directions (e.g. up and down or left and right) away from longitudinal axis (L-L). Multiple production lines may be used because there are a few structural differences between a uni-directional catheter and a bi-directional catheter to achieve this difference in deflection. These differences may include the handle (110) and the deflection mechanism (e.g. the deflection drive assembly).

It may be beneficial to use some of the same components for both uni-directional and bi-directional catheters. This may be beneficial because the same production line may then be used to produce both the uni-directional catheter and the bi-directional catheter. Using the same production line may also save on the time necessary to train assembly operators, reduce the potential for mixing components on the production line, ensure cross-compatibility of assembly operators between uni-directional and bi-directional catheter lines, and generate larger volume discounts during the procurement of the components.

Using the same or similar handle (110) for uni-directional and bi-directional catheters may also provide a physician (PH) greater peace of mind, as the physician (PH) may be more comfortable with the user interface. Catheter assembly (100) captures modifying a bi-direction deflection mechanism to enable uni-directional usage. Conversely, a second exemplary catheter assembly (500) captures modifying a bi-direction deflection mechanism to enable uni-directional usage.

As will be described in greater detail below, exemplary deflection drive assemblies (300, 400, 508, 608) incorporate exemplary rack and pinion assemblies (304, 404, 518, 618) to either (1) transfer rotational motion of a pinion (308, 408) from a rocker arm (230, 501) into linear motion of a rack (306, 406), or (2) transfer linear motion of a rack (524, 624) from a linear slider (514, 614) into rotational motion of a pinion (526, 626). As shown, a single rack (306, 406, 524,

624) interacts with a pinion (308, 408, 526, 626). While the input member is shown as rocker arm (230, 501) in FIGS. 2 and 6-12, the input member is shown and described as linear slider (514, 614) of catheter assembly (500, 600) of FIGS. 13-17. Other suitable input members are also envisioned as will be apparent to those skilled in the art in view of the teachings herein.

Figure 6:
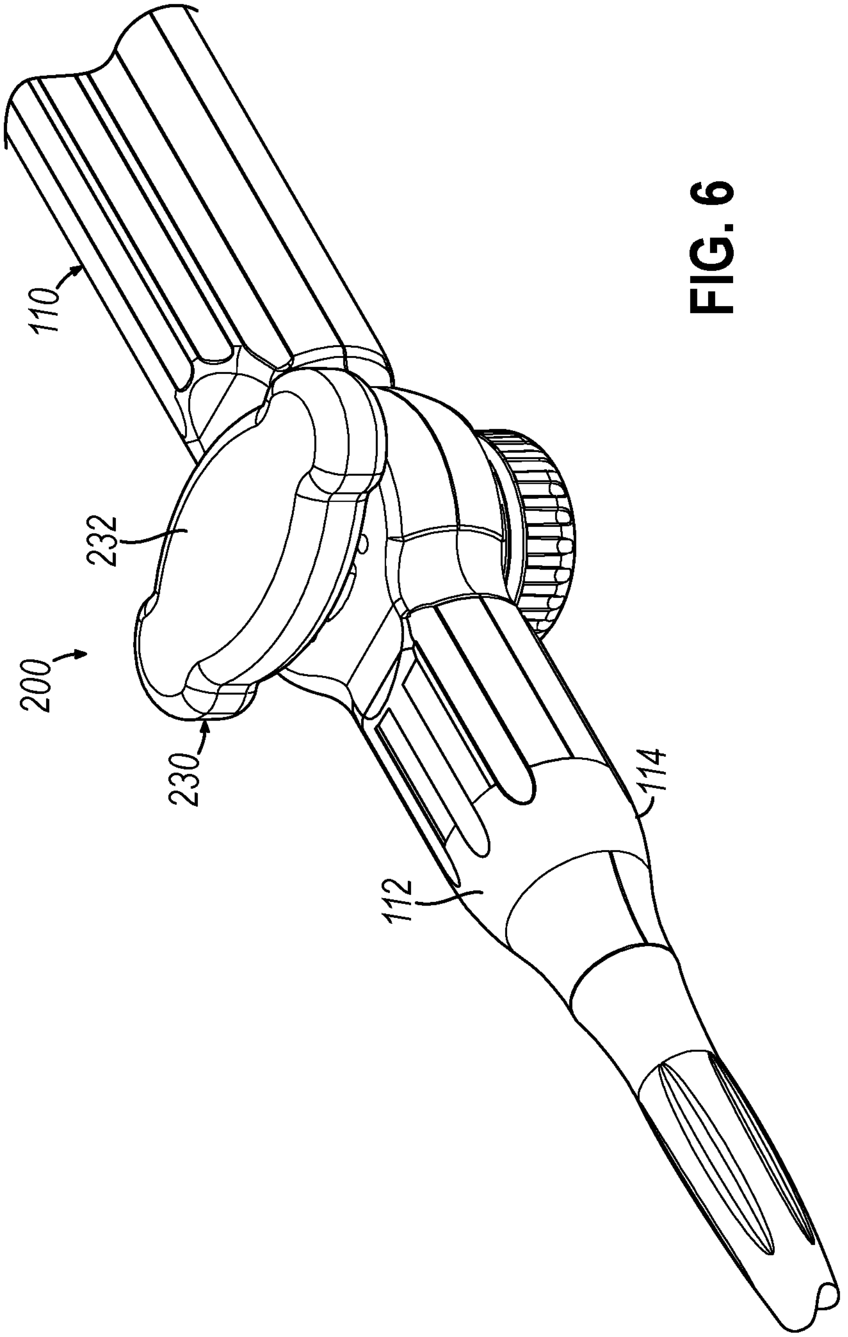
FIG. 6 depicts a perspective view of a handle and a deflection drive assembly of the catheter assembly of FIG. 1, with the deflection drive assembly including a rocker arm.
Figure 7:
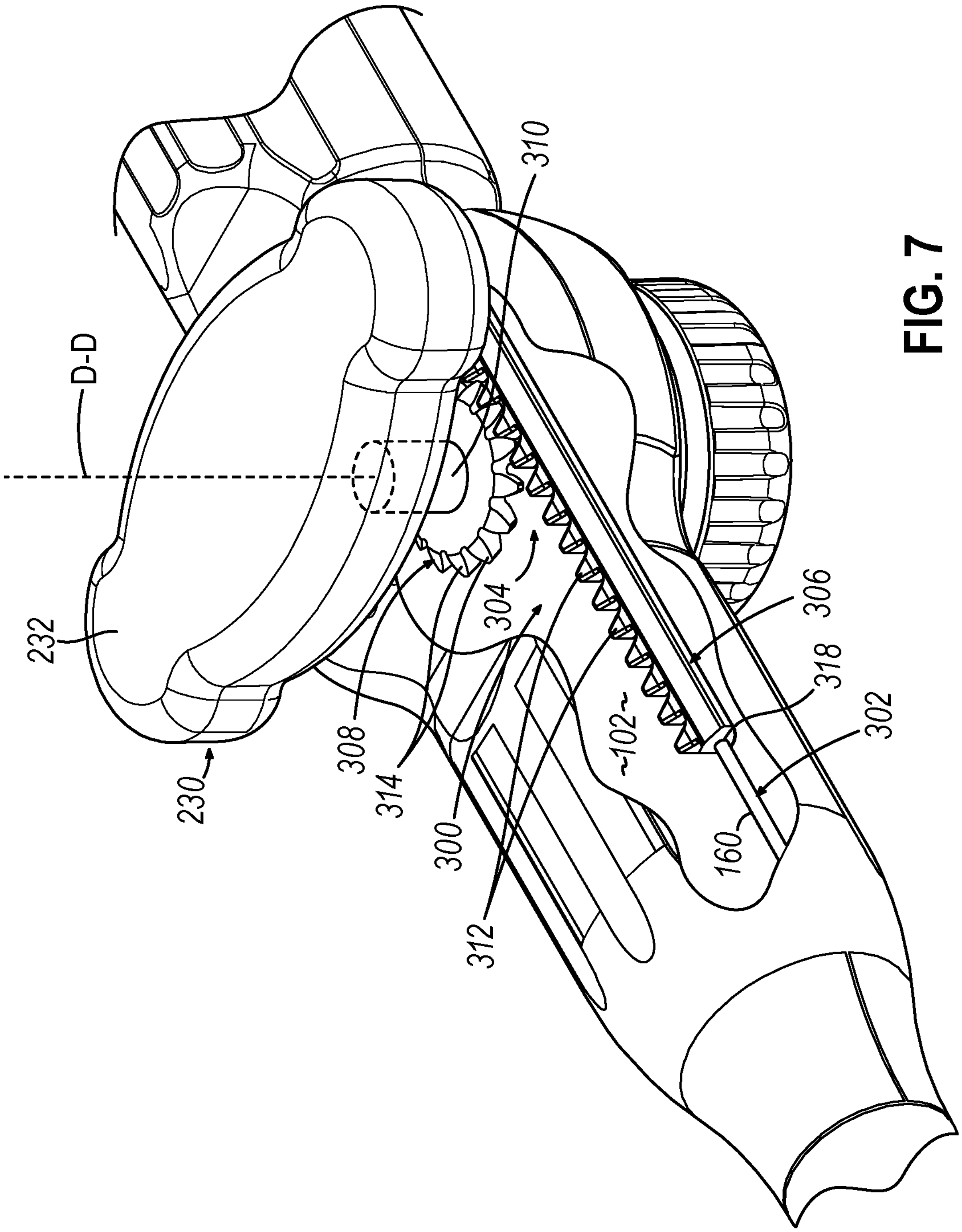
FIG. 7 depicts a schematic perspective view of the handle and the deflection drive assembly of FIG. 6, with a portion of the handle omitted to reveal internal components including a rack and pinion assembly.

A. First Exemplary Catheter Assembly for Bi-Directional End Effector Deflection FIG. 7 shows a schematic perspective view of handle (110) and deflection drive assembly (300) of FIG. 6, with a portion of handle (110) omitted to reveal internal components. As described above, catheter assembly (100) includes handle (110), catheter (120), end effector (140), and deflection drive assembly (300). Catheter (120) extends distally from handle (110). As shown in FIG. 6, handle (110) includes a first casing portion (112) and a second casing portion (114) that together define an internal cavity (102). Rocker arm (230) includes an elongated body (232) for enhanced gripping by the physician (PH). One such suitable example of a rocker arm (230) rotatably actuating a bi-directional catheter is shown and described in U.S. Prov. Pat. App. No. 62/866,109, entitled "Catheter Deflection System with Deflection Load Limiter," filed on Jun. 25, 2019, the disclosure of which is incorporated by reference herein, in its entirety.

Deflection drive assembly (300) is configured to deflect end effector (140) away from longitudinal axis (L-L) defined by a proximal portion of catheter (120). Deflection drive assembly (300) of the present example includes rocker arm (230) associated with handle (110), a translating assembly (302), and a rack and pinion assembly (304) coupled with rocker arm (230). Translating assembly (302) is indirectly or directly coupled with rack and pinion assembly (304) and end effector (140). As shown, translating assembly (302) includes push-pull cable (160). As will be described in greater detail below, the physician (PH) may actuate rocker arm (230) relative to handle (110), such that rack and pinion assembly (304) actuates push-pull cable (160) to selectively deflect end effector (140) laterally away from a longitudinal axis (L-L), thereby enabling the physician (PH) to actively steer end effector (140) within the patient (PA). Rocker arm (230) may drive translating assembly (302) to deflect end effector (140) away at an angle (A) relative to longitudinal axis (L-L) in two directions (up and down or left and right). Rocker arm (230) is configured to rotate relative to handle (110) about drive axis (D-D) without translating along longitudinal axis (L-L). As shown, drive axis (D-D) is perpendicular with longitudinal axis (L-L).

Rack and pinion assembly (304) has a rack (306) and a pinion (308). Only a single rack (306) is shown in FIGS. 7-11B. Rack and pinion assembly (304) converts rotational motion of pinion (308) from rocker arm (230) into linear motion of rack (306). Rack and pinion assembly (304) is coupled with rocker arm (230) and translating assembly (302) using a shaft (310). As shown, rocker arm (230) and pinion (308) are co-axial about drive axis (D-D). Rack (306) is operatively coupled with distal tip member (142) using push-pull cable (160), or another suitable translating member, that drives the uni-directional deflection of distal tip member (142). Rack (306) includes a plurality of teeth (312). Similarly, pinion (308) includes a plurality of teeth (314) configured to selectively engage teeth (312) of rack (306). As will be described in greater detail with reference to FIGS. 8A-8C, deflection drive assembly (300) may optionally include a locking assembly (316). A few suitable examples of locking assemblies will be described; however, other suitable locking assemblies are also envisioned.

As shown, translating assembly (302) has a single push-pull cable (160) that is coupled with rack (306) and end effector (140). Particularly, push-pull cable (160) is coupled with rack (306) at a proximal attachment point (318) using any one of a variety of suitable attachment methods. Similarly, push-pull cable (160) is coupled with end effector (140) at a distal attachment point (321) using any one of a variety of suitable attachment methods. While push-pull cable (160) is generally coupled with rack (306) after rack (306) is engaged with pinion (308), it is also envisioned that push-pull cable (160) may be coupled with rack (306) before rack (306) is engaged with pinion (308). Deflection drive assembly (300) transfers linear motion of rack (306) to either push push-pull cable (160) in a distal direction (see FIG. 9B) or pull push-pull cable (160) in a proximal direction (see FIG. 9C). Particularly, rack and pinion assembly (304) is configured to drive the single push-pull cable (160) in opposing directions using the input from rocker arm (230). While push-pull cable (160) is shown as a stainless-steel rod, other suitable push-pull cables are also envisioned that have sufficient bendability and column strength.

Figure 8A:
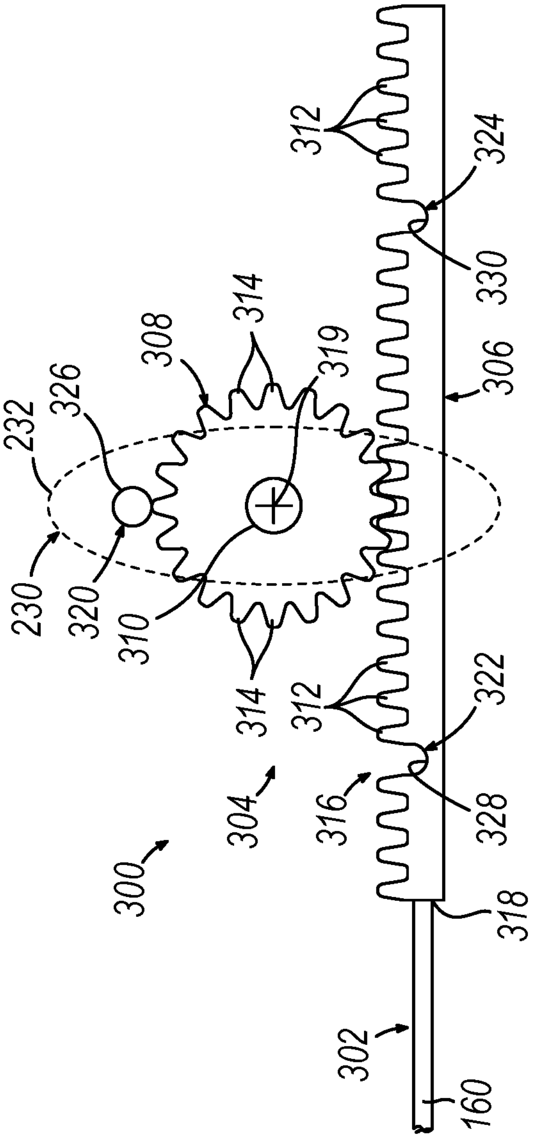
FIG. 8A depicts a top schematic view of the deflection drive assembly of FIG. 6, with the rocker arm and a rack of the rack and pinion assembly in a neutral position for bi-directional deflection, and a first exemplary locking assembly in an unlocked configuration.
Figure 9A:
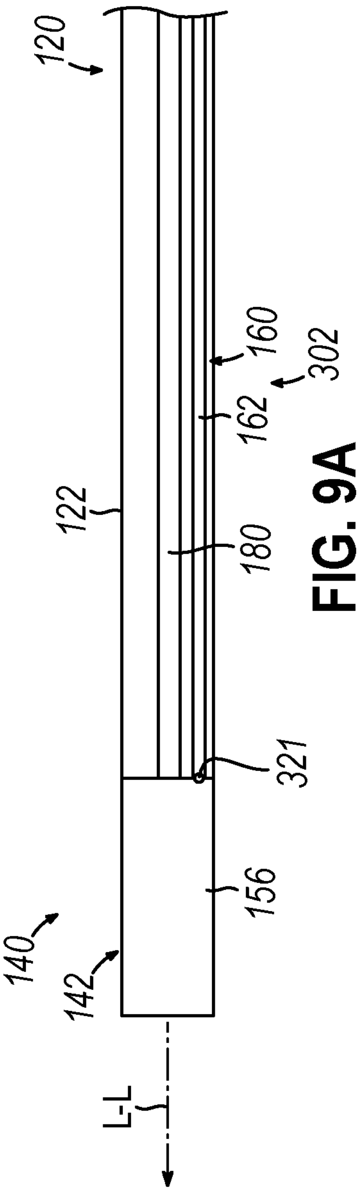
FIG. 9A depicts a top plan view of the distal portion of the catheter of FIG. 1, with a portion of the outer sheath omitted to reveal internal components, where the distal portion of the catheter is in a neutral position associated with the neutral position of the rocker arm of FIG. 8A.
Figure 8B:
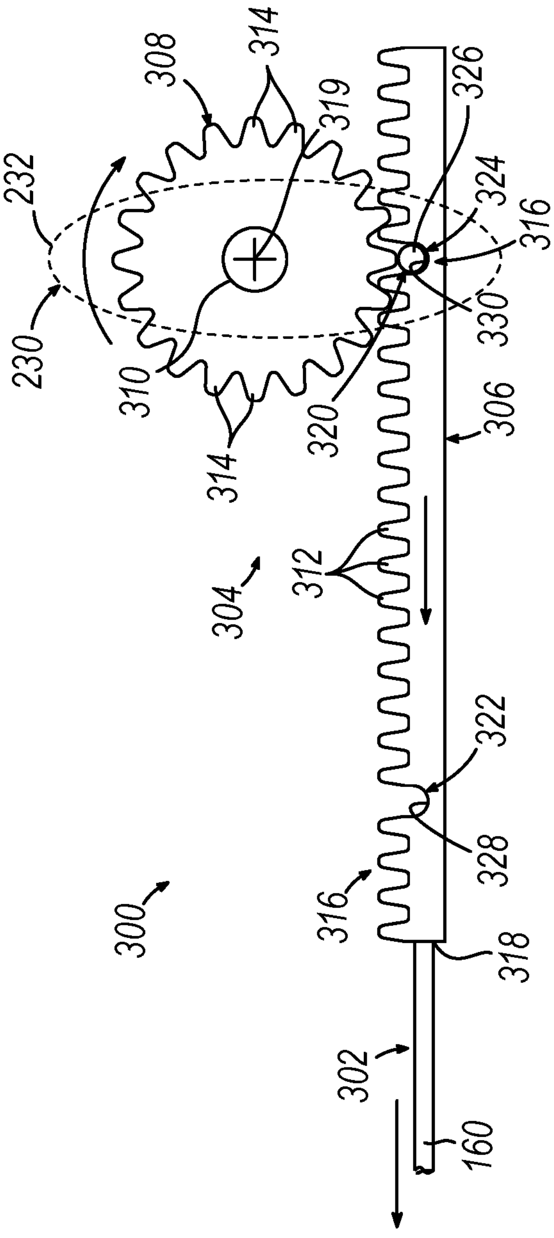
FIG. 8B depicts a top schematic view of the deflection drive assembly of FIG. 8A, but with the rocker arm in a first position, the rack in a first longitudinal position, and the locking assembly in a first locked configuration.
Figure 8C:
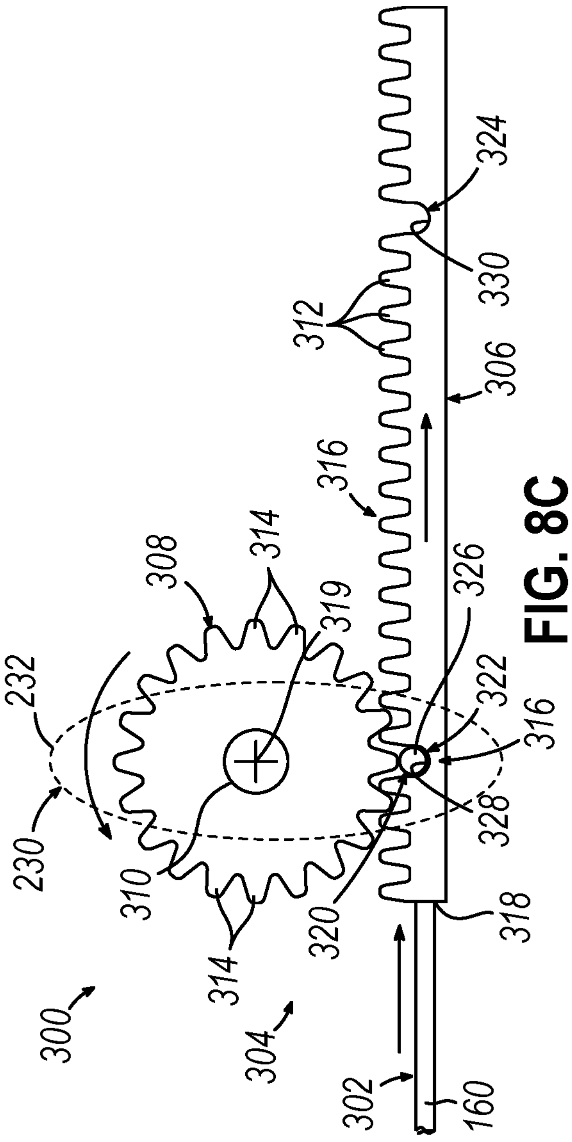
FIG. 8C depicts a top schematic view of the deflection drive assembly of FIG. 8A, but with the rocker arm in a second position, the rack in a second longitudinal position, and the locking assembly in a second locked configuration.

FIGS. 8A-8C show an exemplary use of deflection drive assembly (300) to deflect end effector (140) and the distal portion of catheter (120) about longitudinal axis (L-L). FIGS. 8A and 9A show catheter assembly (100) when end effector (140) is in a neutral non-deflected position. Particularly, FIG. 8A shows a top schematic view of deflection drive assembly (300) of FIG. 6, with rocker arm (230) in a neutral position. Rocker arm (230) is pivotable about a pivot point (319). When rocker arm (230) is in the neutral position, rack (306) of rack and pinion assembly (304) is in a neutral non-deflected position.

Figure 9B:
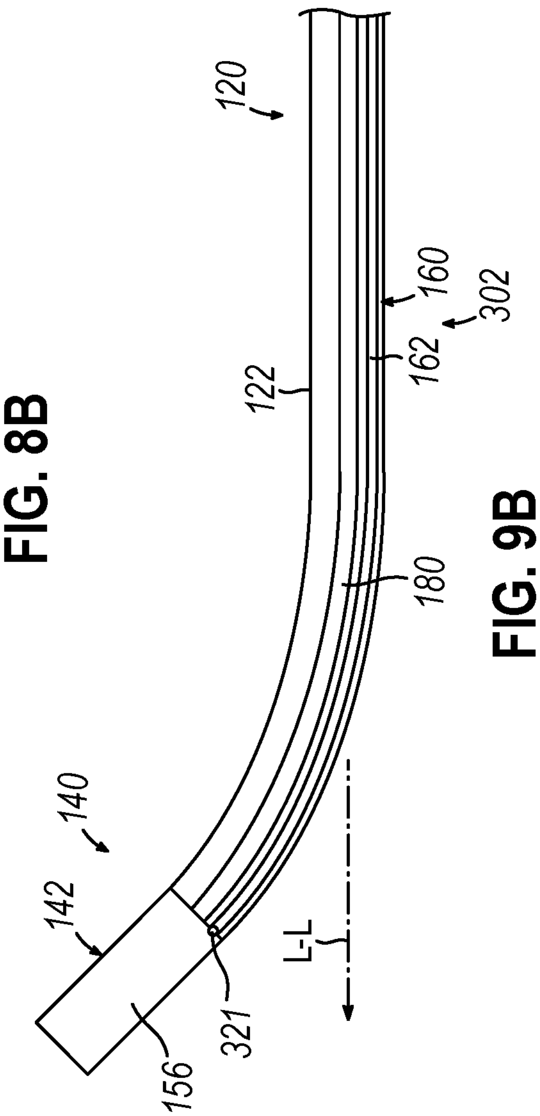
FIG. 9B depicts a top plan view of the distal portion of the catheter of FIG. 1, with a portion of the outer sheath omitted to reveal internal components, where the distal portion of the catheter is in a first deflected position associated with the first position of the rocker arm of FIG. 8B.
Figure 9C:
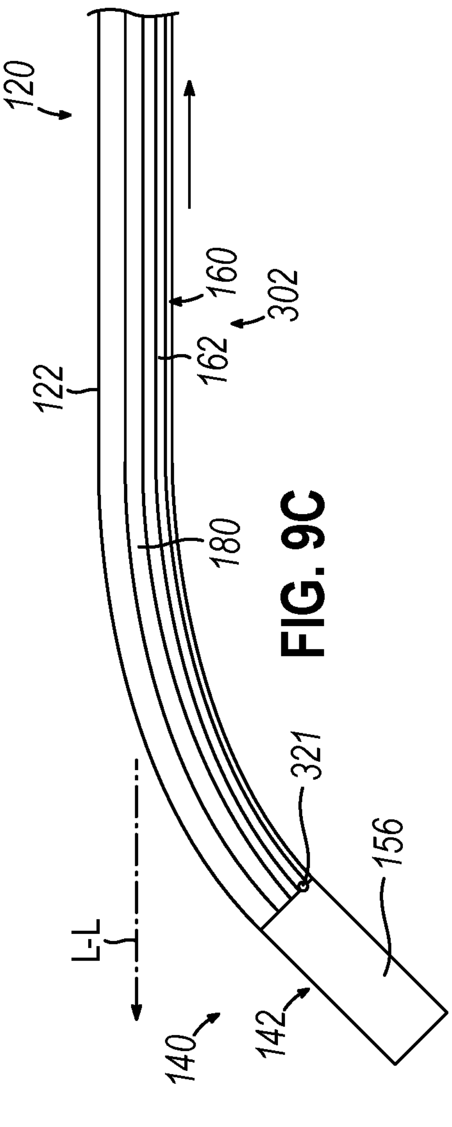
FIG. 9C depicts a top plan view of the distal portion of the catheter of FIG. 1, with a portion of the outer sheath omitted to reveal internal components, where the distal portion of the catheter is in a second deflected position associated with the second position of the rocker arm of FIG. 8C.

FIG. 9A shows a top plan view of distal portion of catheter (120) of FIG. 1, with a portion of outer sheath (122) omitted to reveal internal components. Push-pull cable (160) is in a neutral non-deflected position associated with end effector (140) being in the neutral non-deflected position. As shown in FIGS. 9A-9C, intermediary portion (162) extends proximally from distal end portion (164) through outer sheath (122) of catheter (120). Intermediary portion (162) may include various segments coupled to each other in order to extend to distal end portion (164). Various segments of intermediary portion (162) may be coupled through any suitable means as would be apparent to one skilled in the art in view of the teachings herein.

As shown in FIGS. 8A-8C, locking assembly (316) is interposed between rocker arm (230) and translating assembly (302). FIG. 8A shows the locking assembly (316) in the unlocked configuration, such that end effector (140) may move along a range of angles. In the locked configuration shown in FIGS. 8B and 8C, locking assembly (316) locks end effector (140) at the desired angle relative to longitudinal axis (L-L). Particularly, in FIG. 9B, rack (306) is prevented from moving further distally by locking assembly (316). Locking assembly (316) includes locking features (320, 322, 324) that define the locked configuration and the unlocked configuration. As shown in FIG. 8A, pinion (308) includes locking feature (320). While pinion (308) is shown as only including a single locking feature (320), pinion (308) may include two or more locking features that are spaced about the circumference of pinion (308). Similarly, rack (306) includes locking features (322, 324) that are spaced from one another along longitudinal axis (L-L). As shown, locking features (322, 324) of rack (306) are disposed on either end of the working length of rack (306). Rack (306) may include more or fewer locking features. Locking features (322, 324) of rack (306) are complementary to locking feature (320) of pinion (308). Locking feature (320) is configured to engage one of locking features (322, 324) in the locked configuration.

Locking features (322, 324) are spaced at a distance from locking feature (320) in the unlocked configuration. As shown, locking features (320, 322, 324) are cylindraceous in shape. Particularly, locking feature (320) of pinion (308) is a cylindraceous pin (326), while locking features (322, 324) of rack (306) are cylindraceous detents (328, 330). Cylindraceous pin (326) of locking feature (320) of pinion (308) is configured to removably couple with (e.g. snap into) cylindraceous detents (328, 330) of locking features (322, 324) of rack (306) in the locked configuration. Cylindraceous pin (326) projects downwardly and unitarily from rocker arm (230); adjacent to pinion (308). Cylindraceous pin (326) may be positioned adjacent to the gear tooth tip. Cylindraceous detents (328, 330) may be formed into gear tooth troughs of rack (306).

With same or less amount of resistance using rocker arm (230), cylindraceous pin (326) of pinion (308) is removable from one of cylindraceous detents (328, 330) of rack (306) to unlock the deflection of end effector (140). Cylindraceous pin (326) and cylindraceous detents (328, 330) provide a coupling that is strong enough to resist unintended longitudinal movement of the rack (306) (e.g., in response to lateral forces exerted against the end effector by patient anatomy, etc.) when locking assembly (316) is in the state shown in FIG. 10A or 10B; yet weak enough to enable the operator to intentionally transition the assembly between the states shown in FIGS. 10A and 10B without needing to apply undue torqueing on rocker arm (230). Locking assembly (316) may provide a tactile indication when entering into or exiting from the locked or unlocked configuration. While not shown, a variety of non-cylindraceous shapes are also envisioned for locking features (320, 322, 324), including spherical locking features.

FIG. 8B shows a top schematic view of deflection drive assembly (300) of FIG. 8A, but with rocker arm (230) in a second position (rotated 180 degrees clockwise), rack (306) in a first longitudinal position, and locking assembly (316) in a first locked configuration. As shown in FIG. 8B, the first locked configuration is the distal most position of rack (306). FIG. 9B shows a top plan view of distal portion of catheter (120) of FIG. 1, with a portion of outer sheath (122) omitted to reveal internal components, where distal portion of catheter (120) is in the first deflected position associated with first position of rocker arm (230) of FIG. 8B. As best shown in FIG. 9B, rotation of rocker arm (230) to the first position shown in FIG. 8B drives rack and pinion assembly (304) into a corresponding longitudinal position such that push-pull cable (160) is driven distally. As shown in FIG. 8B, in the first locked configuration, cylindraceous pin (326) of locking feature (320) is disposed in cylindraceous detent (330) of locking feature (324).

When the physician (PH) desires to deflect end effector (140) relative to central longitudinal axis (L-L) to the deflected position shown in FIG. 9C, the physician (PH) may rotate rocker arm (230) relative to handle (110) to the position shown in FIG. 8C. Particularly, FIG. 8C shows a top schematic view of deflection drive assembly (300) of FIG. 8A, but with rocker arm (230) in a second position, rack and pinion assembly (304) in a second longitudinal position; and locking assembly (316) in a second locked configuration. As shown in FIG. 8C, the second locked configuration is the proximal-most position of rack (306). FIG. 9C shows a top plan view of distal portion of catheter (120) of FIG. 1, with a portion of outer sheath (122) omitted to reveal internal components, where distal portion of catheter (120), including irrigation tube (180), is in the deflected position associated in the second position of rocker arm (230). As shown in FIG. 8C, rotation of rocker arm (230) to the rotational position shown in FIG. 8C drives pinion (308) of rack and pinion assembly (304) into a corresponding rotational position such that rack (306) and push-pull cable (160) move proximally. As shown in FIG. 8C, in the second locked configuration, cylindraceous pin (326) of locking feature (320) is disposed in cylindraceous detent (328) of locking feature (322). It is envisioned that the physician (PH) may rotate rocker arm (230) to move end effector (140) from the position shown in FIG. 8A to the position shown in FIG. 8C, without rotating rocker arm (230) to the position shown in FIG. 8B.

B. First Exemplary Catheter Assembly for Uni-Directional End Effector Deflection It may be desirable to modify deflection drive assembly (300) that is configured to provide bi-directional deflection to end effector (140) as shown in FIGS. 8A-9C to instead provide uni-directional deflection to end effector (140) as shown in FIGS. 10A-11B. This switch from bi-directional deflection to uni-directional deflection of end effector (140) may be achieved while deflection drive assembly (300) is being manufactured (e.g. being assembled) by modifying the neutral position of deflection drive assembly (300). For example, as shown in FIGS. 10A-11B, this may be obtained by modifying the initial position of rack and pinion assembly (304) and the longitudinal position at which translating assembly (302) is coupled with rack and pinion assembly (304).

Figure 10A:
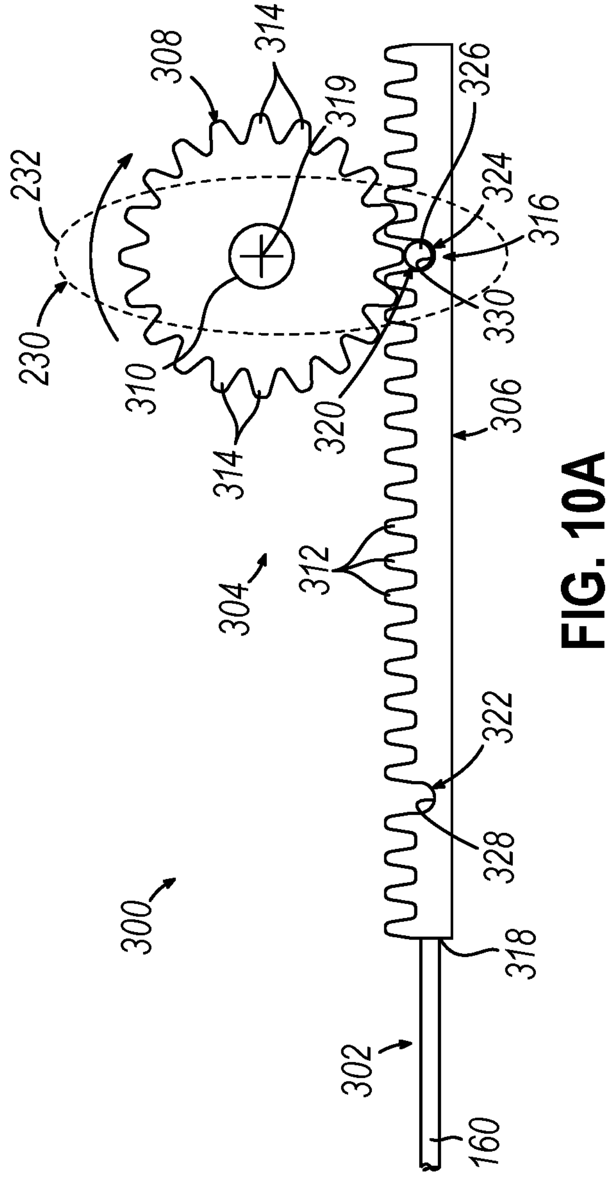
FIG. 10A depicts a top schematic view of the deflection drive assembly of FIG. 6, with the rocker arm and the rack of the rack and pinion assembly in a neutral position for unidirectional deflection, and the locking assembly in a first locked configuration.
Figure 11A:
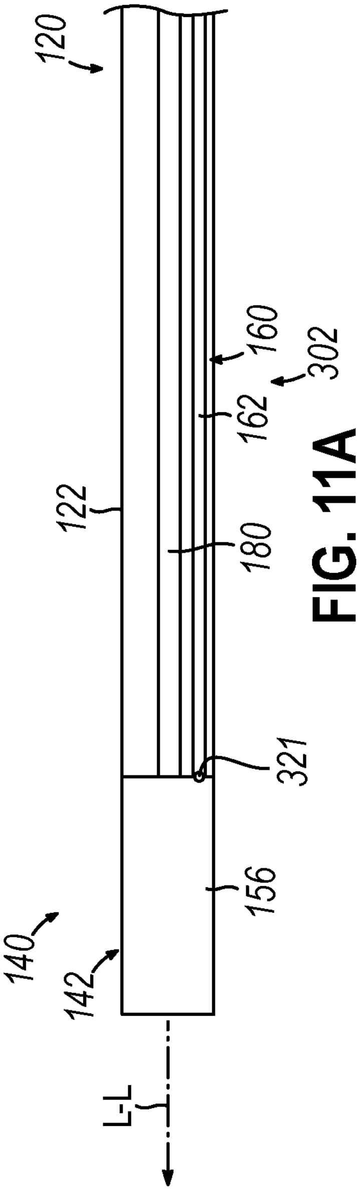
FIG. 11A depicts a top plan view of the distal portion of the catheter of FIG. 1, with a portion of the outer sheath omitted to reveal internal components, where the distal portion of the catheter is in a non-deflected position associated with the rocker arm in the neutral position of FIG. 10A.

FIG. 10A shows a top schematic view of deflection drive assembly (300) of FIG. 8A, but with rocker arm (230) in a neutral non-deflected position, rack (306) in a first longitudinal position, and locking assembly (316) in a first locked configuration. FIG. 11A shows a top plan view of distal portion of catheter (120) of FIG. 1, with a portion of outer sheath (122) omitted to reveal internal components, where distal portion of catheter (120) is in the neutral non-deflected position. As shown in FIG. 10A, rack and pinion assembly (304) is adjusted from the neutral configuration shown in FIG. 8A to the neutral configuration shown in FIG. 10A; and the longitudinal position at which push-pull cable (160) is fixedly secured to rack (306) is adjusted from the neutral position shown in FIG. 8A to the neutral position shown in FIG. 10A. As shown in FIG. 10A, locking assembly (316) in the first locked configuration prevents rack (306) from being driven distally. In the first locked configuration, cylindraceous pin (326) of locking feature (320) is disposed in cylindraceous detent (330) of locking feature (324).

Figure 10B:
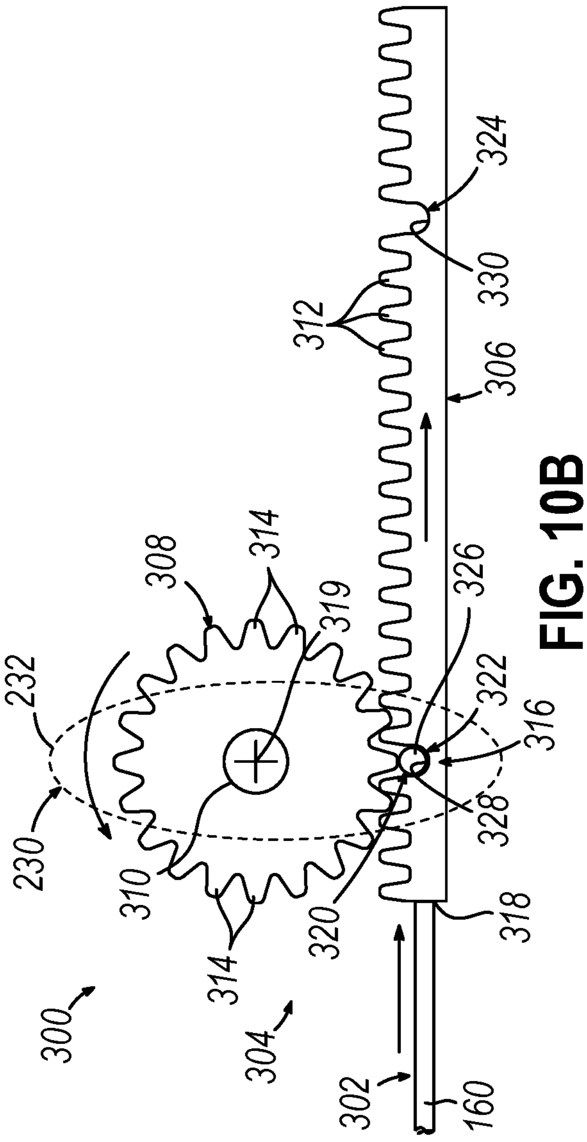
FIG. 10B depicts a top schematic view of the deflection drive assembly of FIG. 10A, but with the rocker arm in a first rotational position, the rack in a first longitudinal position, and the locking assembly in a second locked configuration.
Figure 11B:
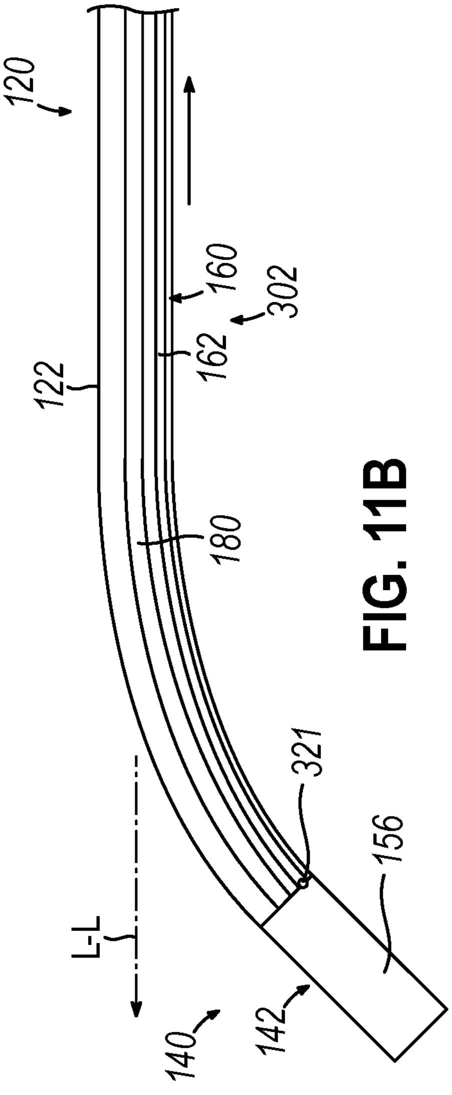
FIG. 11B depicts a top plan view of the distal portion of the catheter of FIG. 1, with a portion of the outer sheath omitted to reveal internal components, where the distal portion of the catheter is in the deflected position associated with the first position of the rocker arm of FIG. 10B.

FIG. 10B shows a top schematic view of deflection drive assembly (300) of FIG. 10A, but with rocker arm (230) in a first rotated position, rack (306) moved to a first longitudinal position, and the locking assembly (316) in a second locked configuration. FIG. 11B shows a top plan view of the distal portion of the catheter (120) of FIG. 1, with a portion of the outer sheath (122) omitted to reveal internal components, where the distal portion of catheter (120) is in the deflected position associated with the first position of the rocker arm (230) of FIG. 10B. As shown in FIG. 11B, rotation of rocker arm (230) from the position shown in FIG. 10A to the position shown in FIG. 10B drives rack and pinion assembly (304) into a corresponding rotational position such that push-pull cable (160) is driven proximally. While not necessarily shown in the present drawings, it should be understood that the distal portion of catheter (120) may achieve a greater degree of lateral deflection (i.e., larger bend angle) with the arrangement shown in FIGS. 10A-11B than with the arrangement shown in FIGS. 8A-9C.

C. Second Exemplary Locking Assembly

Figure 12:
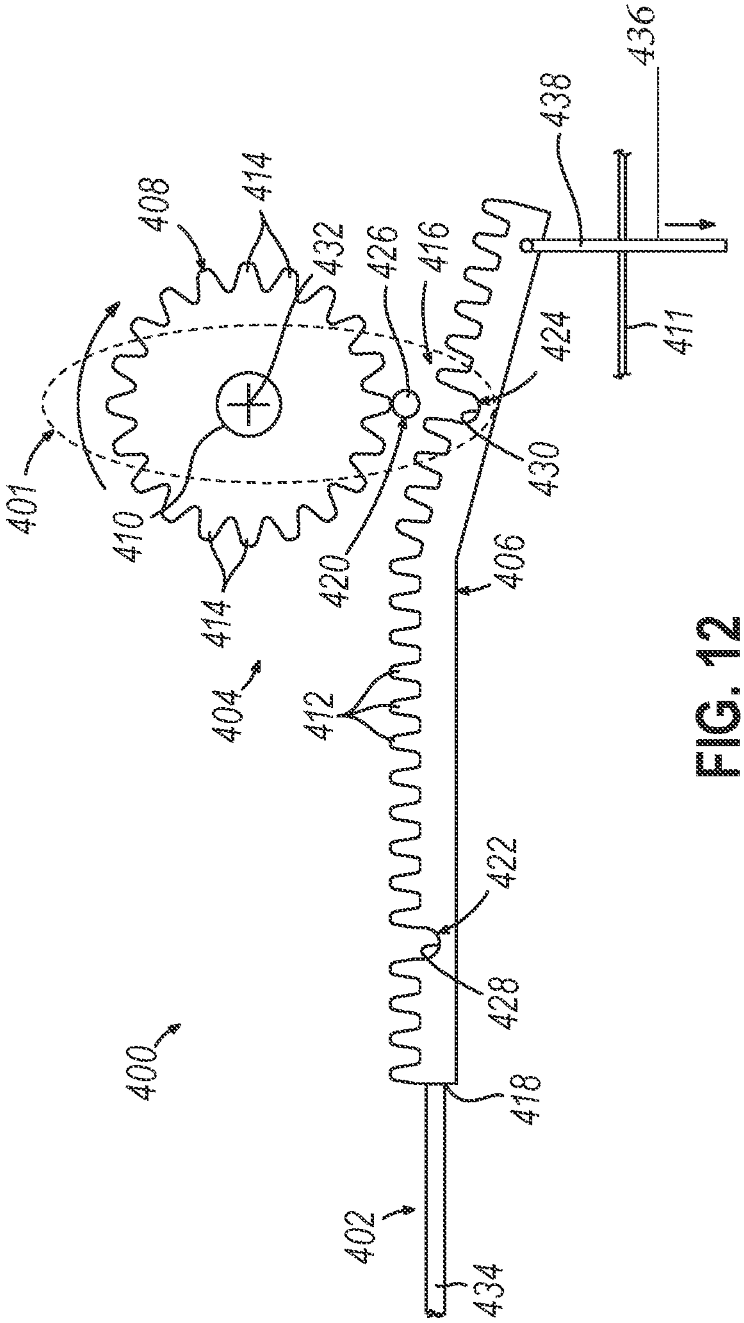
FIG. 12 depicts a top schematic view of a second exemplary deflection drive assembly, with a second exemplary locking assembly in an unlocked configuration.

FIG. 12 shows a top schematic view of a second exemplary deflection drive assembly (400), with a second exemplary locking assembly (416) in an unlocked configuration. Deflection drive assembly (400) includes a rocker arm (401) similar to rocker arm (230), a translating assembly (402) similar to translating assembly (302), and a rack and pinion assembly (404) similar to rack and pinion assembly (304). Rack and pinion assembly (404) includes a rack (406) and a pinion (408). Rack (406) includes teeth (412), and pinion (408) includes teeth (414). Rack (406) is coupled with a push-pull cable (434) of translating assembly (402) at an attachment point (418) similar to proximal attachment point (318). Locking assembly (416) includes a locking feature (420) on pinion (408) and locking features (422, 424) on rack (406). For example, locking feature (422) is shown as a cylindraceous pin (426) projects downwardly and unitarily from rocker arm (230); adjacent to pinion (408). Cylindraceous pin (426) may be positioned adjacent to the gear tooth tip. Locking features (422, 424) are cylindraceous detents (428, 430) formed in gear tooth troughs respectively. Rocker arm (401) may be coupled with pinion (408) using a shaft (410). Shaft (410) may be fixably coupled to one or both of rocker arm (401) and pinion (408).

Locking assembly (416) may include a biasing member (438) configured to bias rack (406) away from pinion (408) to convert locking assembly (416) from the locked configuration to the unlocked configuration. For example, rack (406) may be formed from a bendable material (e.g. a polymeric material). As shown, biasing member (438) projects outwardly from handle (411), such that biasing member (438) may be manually actuated by the physician (PH). It is envisioned that latching pin (436) or biasing member (438) may be used alone or in combination.

D. Exemplary Catheter Assembly for Exemplary Catheter Assembly for Bi-Directional End Effector Deflection with Third Exemplary Locking Assembly A catheter assembly including a translatable actuator (e.g. a linear slider) may be normally configured to only provide uni-directional deflection of end effector (140). It may be desirable to produce a catheter assembly including a linear slider that is capable of providing bi-directional deflection of end effector (140). Additionally, it may be desirable to use the same production line to produce both the uni-directional catheter including a linear slider and the bi-directional catheter including a linear slider. As previously described, using the same production line for uni-directional and bi-directional catheters may also save on the time necessary to train assembly operators, reduce the potential for mixing components on the production line, ensure cross-compatibility of assembly operators between uni-directional and bi-directional catheter production lines, and generate larger volume discounts during the procurement of the components. For at least these reasons, a second exemplary catheter assembly (500) includes an input member (shown as a linear slider (514)) that is capable of providing bi-directional deflection to an end effector (504). Bi-directional deflection provides a greater range of deflection angles to end effector (504) as compared to uni-directional deflection.

Figure 13:
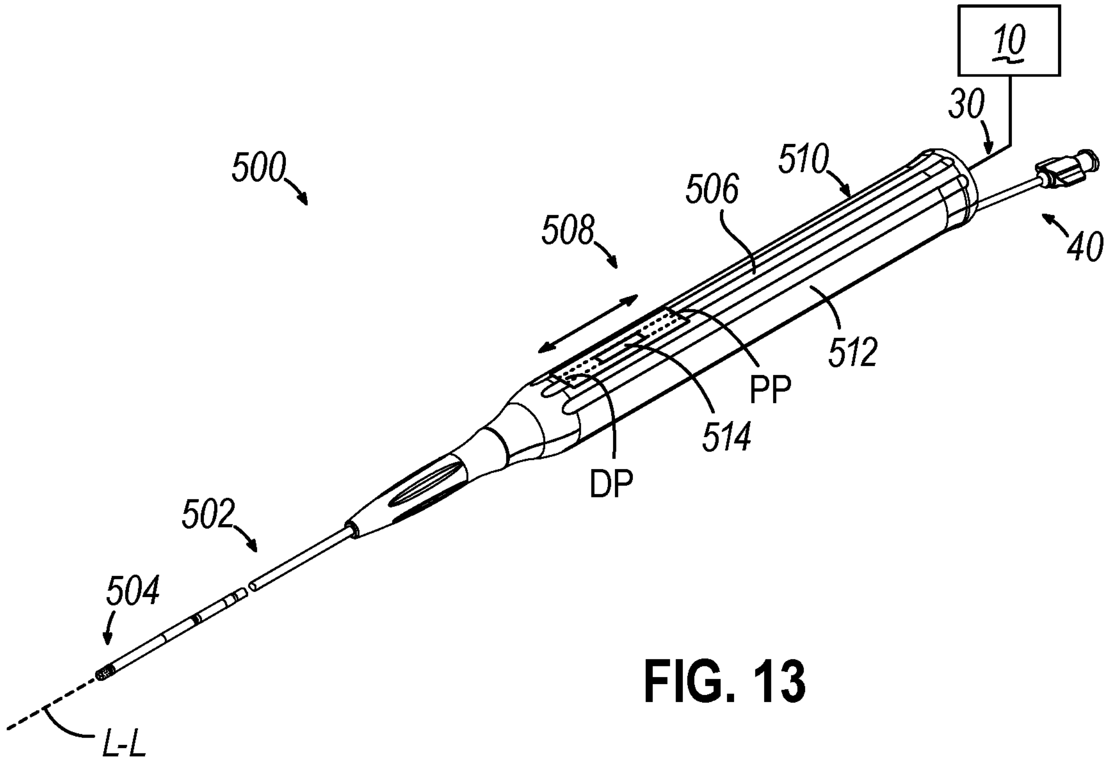
FIG. 13 depicts a perspective view of a second exemplary catheter assembly similar to the catheter assembly of FIG. 1 and including a second exemplary catheter, and a third exemplary deflection drive assembly with additional components shown in schematic form.

FIG. 13 shows a perspective view of catheter assembly (500) similar to catheter assembly (100) of FIG. 1, with additional components shown in schematic form. Catheter assembly (500) includes a second exemplary catheter (502) similar to catheter (120), an end effector (504) similar to end effector (140), a handle (506) similar to handle (110), and a third exemplary deflection drive assembly (508). Handle (506) includes first and second casing portions (510, 512). Deflection drive assembly (508) includes linear slider (514), a translating assembly (516), and a rack and pinion assembly (518). Linear slider (514) is slidable by the physician (PH) along longitudinal axis (L-L) between a distal most position (DP) shown in phantom and a proximal most position (PP) also shown in phantom, as well as any position between the distal most position (DP) and the proximal most position (PP). As shown, linear slider (514) translates along longitudinal axis (L-L) without rotating.

Translating assembly (516) includes a push-pull cable (520). Push-pull cable (520) and an irrigation tube (521), similar to irrigation tube (180), may extend along the length of catheter (120) to reach end effector (504). Cable (30) couples catheter assembly (500) with drive system (10) described above. Wires, similar to wires (32) of FIG. 3, of cable (30) extend along the length of catheter (502) to reach the proximal-most proximal spacer. Wires (32) may be contained within an outer sheath (522), similar to outer sheath (122). Wires (32) may be physically and electrically coupled with the proximal-most proximal spacer in any suitable fashion.

Catheter assembly (500) is configured to enable irrigation fluid to be communicated from a fluid source, similar to fluid source (42) of FIG. 3, to catheter (502) via fluid conduit (40), thereby providing expulsion of the irrigation fluid via openings, similar to openings (158) of FIG. 3, of a distal tip member (523). Similar to distal tip member (142), distal tip member (523) includes a cylindraceous body (540) (see FIGS. 16A-16C) with a dome tip. In the present example, the fluid path for the irrigation fluid includes irrigation tube (521). The proximal end of irrigation tube (521) is coupled with fluid conduit (40) (e.g., at handle (506) of catheter assembly (500)). Irrigation tube (541) extends along the length of catheter (502) to reach end effector (504). In some versions, irrigation fluid may be communicated from the distal end of irrigation tube (541) through the central passageway, ultimately reaching the interior of distal tip member (523) via an aperture, similar to aperture (218).

Figure 14:
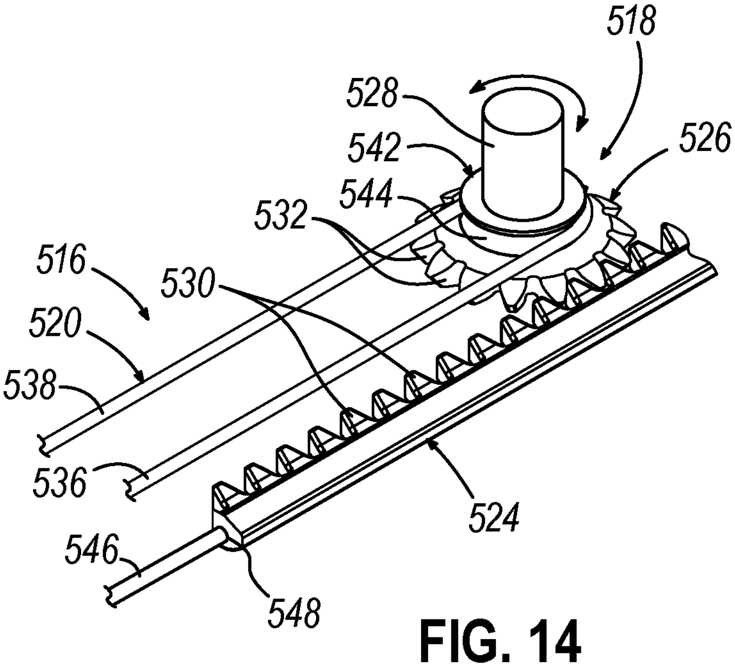
FIG. 14 depicts a perspective view of the deflection drive assembly of FIG. 13, the deflection drive assembly including a third exemplary rack and pinion assembly, a push-pull cable, and a third exemplary locking assembly.

FIG. 14 shows a perspective view of deflection drive assembly (508) of FIG. 13. Rack and pinion assembly (518), similar to rack and pinion assembly (304), includes a rack (524) and a pinion (526). As shown, linear slider (514) is fixably coupled with rack (524). Rack and pinion assembly (518) converts linear motion of rack (524), obtained from linear movement of linear slider (514), into rotational motion of pinion (526). Pinion (526) extends from a shaft (528). Rack (524) includes a plurality of teeth (530). Similarly, pinion (308) includes a plurality of teeth (532) configured to selectively engage teeth (530) of rack (524). Push-pull cable (520) has portions (536, 538). Rack (524) is connected to distal tip member (523) via push-pull cable (520) or another suitable translating member that drives the bi-directional deflection of distal tip member (523).

With continued reference to FIG. 14, deflection drive assembly (508) includes a pulley wheel (542) that is co-axial with pinion (526) of rack and pinion assembly (518). Pulley wheel (542) is rotatably coupled with pinion (526) using shaft (528). Pulley wheel (542) includes an interface surface (544) configured to frictionally engage push-pull cable (520). As will be described in greater detail with reference to FIGS. 15A-16C, handle (110) uses rack and pinion assembly (518) to convert the linear motion of the linear slider (514) into rotational motion of pinion (526) synced with push-pull cable (520) through pulley wheel (542) to deflect distal tip member (523). Distal tip member (523) deflects in multiple directions while providing tension on one of portions (536, 538) of push-pull cable (520) and relieving tension on the other of portions (536, 538) of push-pull cable (520).

Figure 15A:
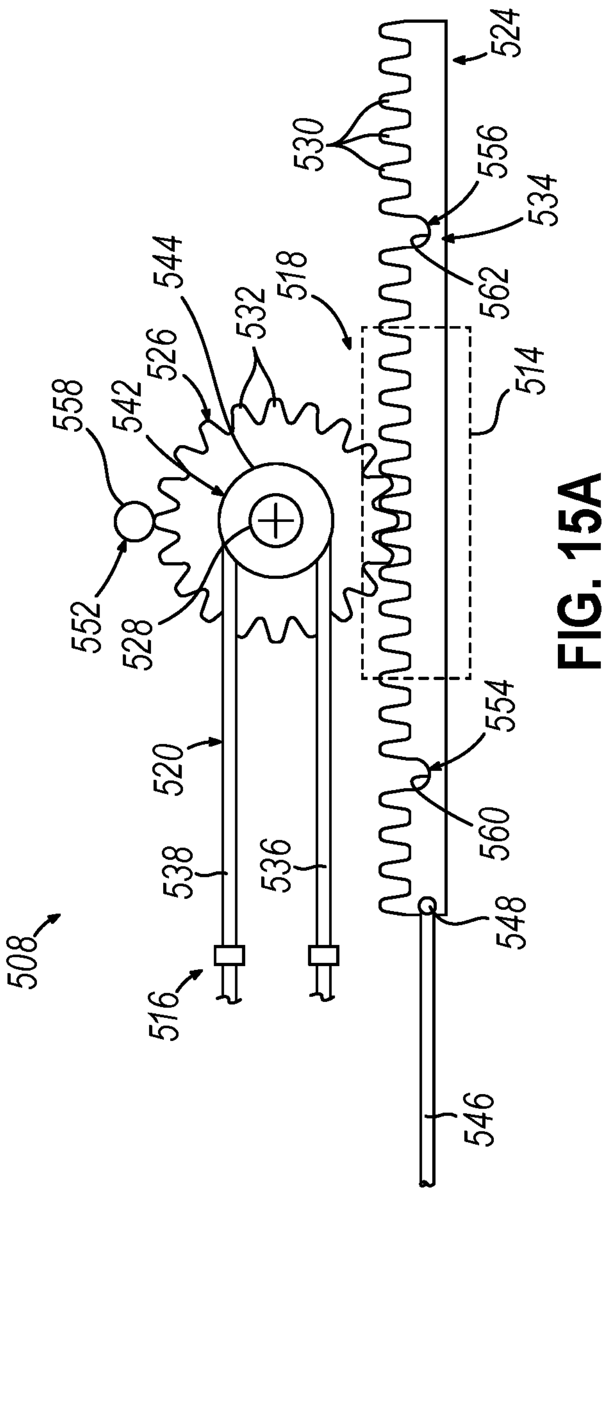
FIG. 15A depicts a top schematic view of the deflection drive assembly of FIG. 14, with the linear slider in a first longitudinal position, the rack of the rack and pinion assembly in a first longitudinal position, and the locking assembly in an unlocked configuration.

FIGS. 15A-16C show exemplary use of deflection drive assembly (508) to deflect end effector (504) and the distal portion of catheter (502) about central longitudinal axis (L-L). FIG. 15A shows a top schematic view of deflection drive assembly (508) of FIG. 14. As shown, linear slider (514) is in a first longitudinal position (i.e. a neutral position), rack and pinion assembly (304) is in a first longitudinal position (i.e. a neutral position), and a third exemplary locking assembly (534) is in an unlocked configuration. While the shown neutral position has pinion (526) disposed in the center of rack (524), the neutral position may have pinion (526) disposed more proximally or more distally along rack (524). As shown in FIG. 15A, pinion (526) and pulley wheel (542) are coaxial with each other and laterally offset from each other. Pinion (526) and pulley wheel (542) may be rotatably coupled together via shaft (528) or be formed together as a unitary piece. For example, pinion (526), shaft (528), and pulley wheel (542) may be formed of plastic, metal, or another suitable material or combination of materials. Push-pull cable (520) is shown as being wrapped around pulley wheel (542). A distal portion of rack (524) may be coupled with a wire (546) at an attachment point (548) for unidirectional deflection of end effector (504), which is not generally omitted for unidirectional deflection of end effector (504).

As shown in 15A-15C, deflection drive assembly (300) may optionally include locking assembly (534) similar to locking assembly (316). Locking assembly (534) includes locking features (552, 554, 556) that define the locked configuration and the unlocked configuration. As shown in FIG. 15A, pinion (526) includes locking feature (552). While pinion (526) is shown as only including a single locking feature (552), pinion (526) may include two or more locking features. Similarly, rack (524) includes locking features (554, 556) that are spaced from one another along longitudinal axis (L-L). As shown, locking features (554, 556) of rack (524) are disposed on either end of the working length of rack (524). Rack (524) may include more or fewer locking features. Locking features (554, 556) of rack (524) are complementary to locking feature (552) of pinion (526). Locking feature (552) is configured to engage one of locking features (554, 556) in the locked configuration.

Locking features (554, 556) are spaced at a distance from locking feature (552) in the unlocked configuration. In other words, in the unlocked position of FIG. 15A, locking features (554, 556) of rack (524) are not engaged with locking feature (552) of pinion (526). As shown, locking features (552, 554, 556) are cylindraceous in shape. Particularly, locking feature (552) of pinion (526) is a cylindraceous pin (558), while locking features (554, 556) of rack (524) are cylindraceous detents (560, 562). Cylindraceous pin (558) of locking feature (552) of pinion (526) is configured to removably couple with (e.g. snap into) cylindraceous detents (560, 562) of locking features (554, 556) of rack (524) in the locked configurations. Cylindraceous pin (558) may be positioned adjacent to the gear tooth tip. Alternatively, the cylindraceous pin (558) may project unitarily from pulley wheel (542); which is rotatably coupled to pinion (526). Cylindraceous detents (560, 562) may be formed into gear tooth troughs of rack (524). With same or less amount of resistance using linear slider (514), cylindraceous pin (558) of pinion (526) is removable from one of cylindraceous detent (560, 562) of rack (524) to unlock the deflection of end effector (504). As such, locking assembly (534) may provide a tactile indication when entering or exiting the locked and unlocked configuration. While not shown, a variety of non-cylindraceous shapes are also envisioned for locking features (552, 554, 556).

Figure 16A:
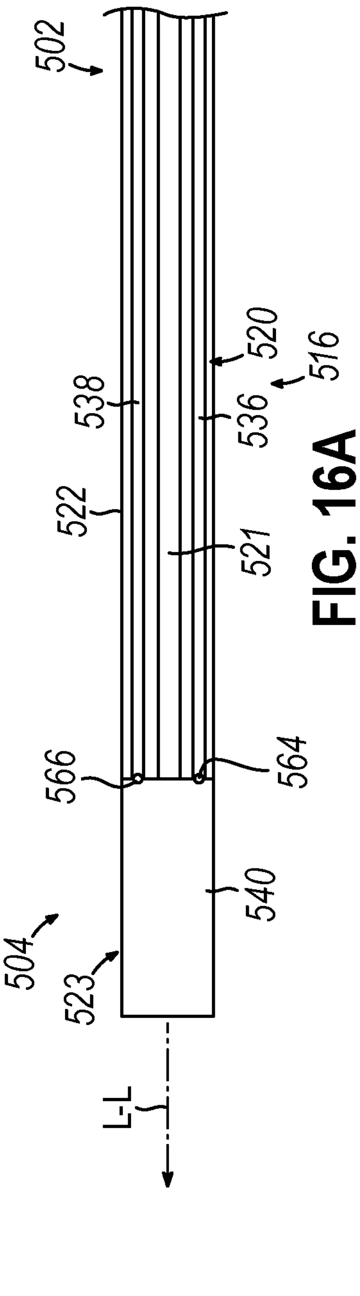
FIG. 16A depicts a top plan view of the distal portion of the catheter of FIG. 13, with a portion of the outer sheath omitted to reveal internal components, where the distal portion of the catheter is in a non-deflected position associated with the first longitudinal position of the linear slider of FIG. 15A.

FIG. 16A shows a top plan view of distal portion of catheter of FIG. 13, with a portion of outer sheath (522) omitted to reveal internal components, where distal portion of catheter (502) is in a neutral non-deflected position associated with first longitudinal position of linear slider (514) of FIG. 15A. As such, FIG. 16A shows catheter assembly (500) when end effector (504) is in the neutral non-deflected position. Likewise, push-pull cable (520) is in a first position associated with end effector (504) being in the non-deflected position. Portion (536) of push-pull cable (520) is coupled at an attachment point (564) with distal tip member (523) of end effector (504). Similarly, portion (538) of push-pull cable (520) is coupled at an attachment point (566) with distal tip member (523) of end effector (504). Since end effector (504) is shown in the neutral non-deflected position, attachment point (564) is disposed at generally the same longitudinal position along longitudinal axis (L-L) as attachment point (566).

Figure 15B:
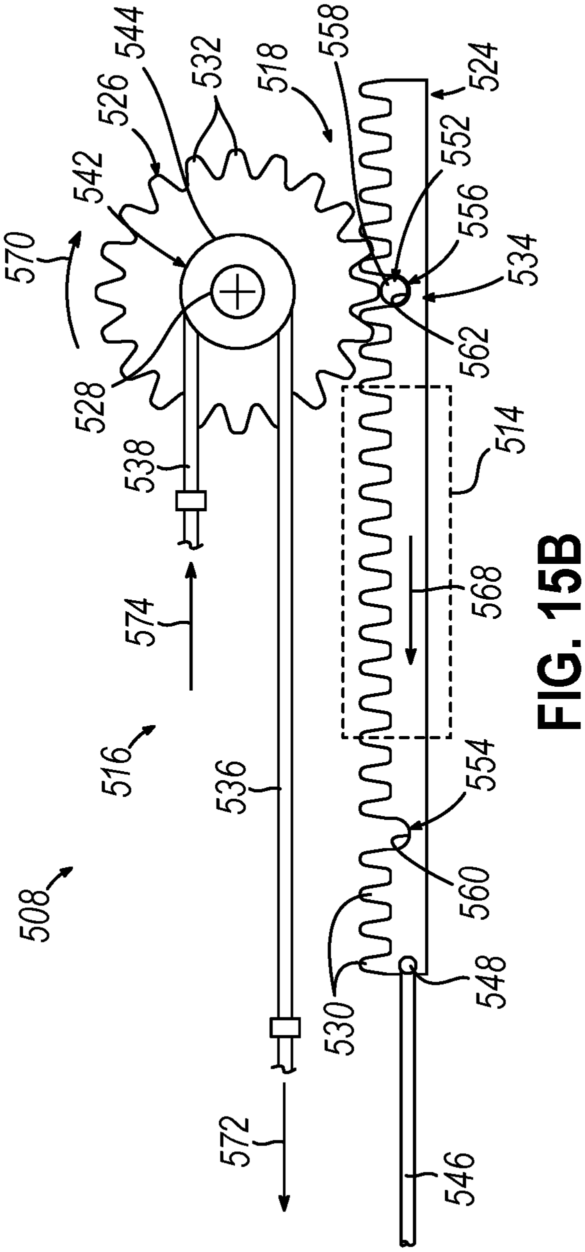
FIG. 15B depicts a top schematic view of the deflection drive assembly of FIG. 15A, but with the linear slider in a second longitudinal position, the rack of the rack and pinion assembly in a second longitudinal position, and the locking assembly in a first locked configuration.

FIG. 15B shows a top schematic view of deflection drive assembly (508) of FIG. 15A. As shown, linear slider (514) is in a second longitudinal position, rack and pinion assembly (304) is in a second longitudinal position, and locking assembly (534) is in a first locked configuration. As shown in FIG. 15B, linear slider (514) is actuated distally (shown by arrow (568)), which drives rack (524) distally along longitudinal axis (L-L). As shown in FIG. 15B, the first locked configuration is the proximal most position of rack (524). The longitudinal motion of rack (524) causes pinion (526) to rotate in a clockwise direction (shown by arrow (570)), since teeth (530) of rack (524) are engaged with teeth (532) of pinion (526). The clockwise rotation of pinion (526) drives clockwise rotation of pulley wheel (542), since pinion (526) and pulley wheel (542) are rotatably coupled. For example, pinion (526) and pulley wheel (542) may be integral with each other or otherwise unitarily secured together. Clockwise rotation of pulley wheel (542) drives clockwise rotation of push-pull cable (520). Particularly, portion (536) of push-pull cable (520) is pushed in a distal direction (shown by arrow (572)) and portion (538) of push-pull cable (520) is pulled in a proximal direction (shown by arrow (574)). As shown in FIG. 15B, in the first locked configuration, cylindraceous pin (558) of locking feature (552) is disposed in cylindraceous detent (562) of locking feature (556).

Alternatively, it is also envisioned that pulley wheel (542) may be substituted for a sprocket, and at least a portion of push-pull cable (520) (e.g., the portion that would directly engage the sprocket during operation) be substituted for a chain, such that the chain may be wrapped around the sprocket, with first and second push-pull cables being joined to each end of the chain. In such an alternative arrangement utilizing a chain and sprocket arrangement, first and second push pull cables move in opposite directions along longitudinal axis (L-L) in a manner similar to the bi-directional catheter shown and described in U.S. Prov. Pat. App. No. 62/866,109, entitled "Catheter Deflection System with Deflection Load Limiter," filed on Jun. 25, 2019, the disclosure of which is incorporated by reference herein, in its entirety.

Figure 16B:
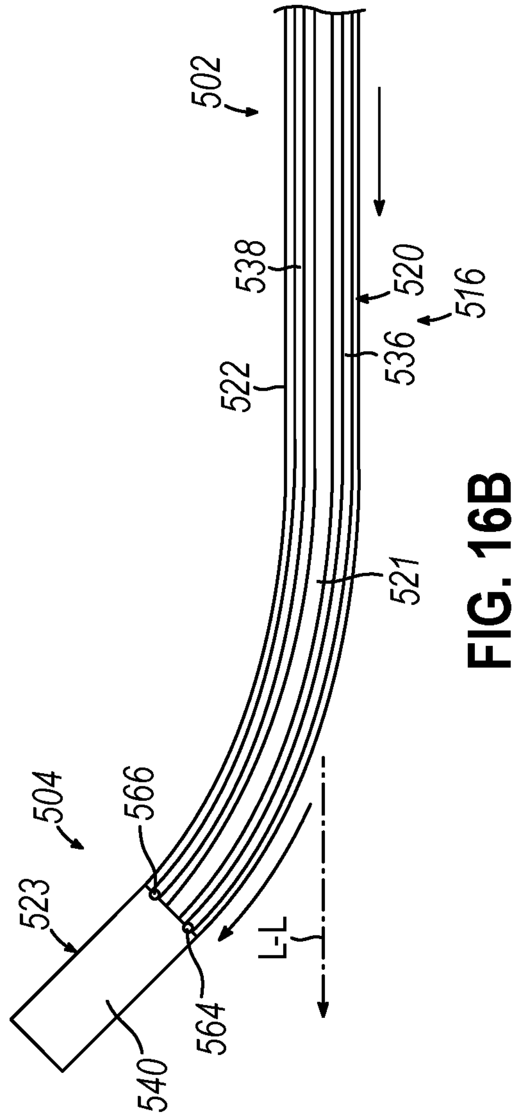
FIG. 16B depicts a top plan view of the distal portion of the catheter of FIG. 13, with a portion of the outer sheath omitted to reveal internal components, where the distal portion of the catheter is in a first deflected position associated with the second longitudinal position of the linear slider of FIG. 15B.

FIG. 16B shows a top plan view of distal portion of catheter (502) of FIG. 13, with a portion of outer sheath (522) omitted to reveal internal components. As shown, distal portion of catheter (502) is in a first deflected position associated with second longitudinal position of linear slider (514) of FIG. 15B. When the physician (PH) desires to deflect end effector (504) in a first direction relative to central longitudinal axis (L-L) to the first deflected position shown in FIG. 16B, the physician (PH) may translate linear slider (514) relative to handle (506) to the position shown in FIG. 15B. Since end effector (504) is shown in the first deflected position, attachment point (564) is disposed distal to attachment point (566) along longitudinal axis (L-L).

Figure 15C:
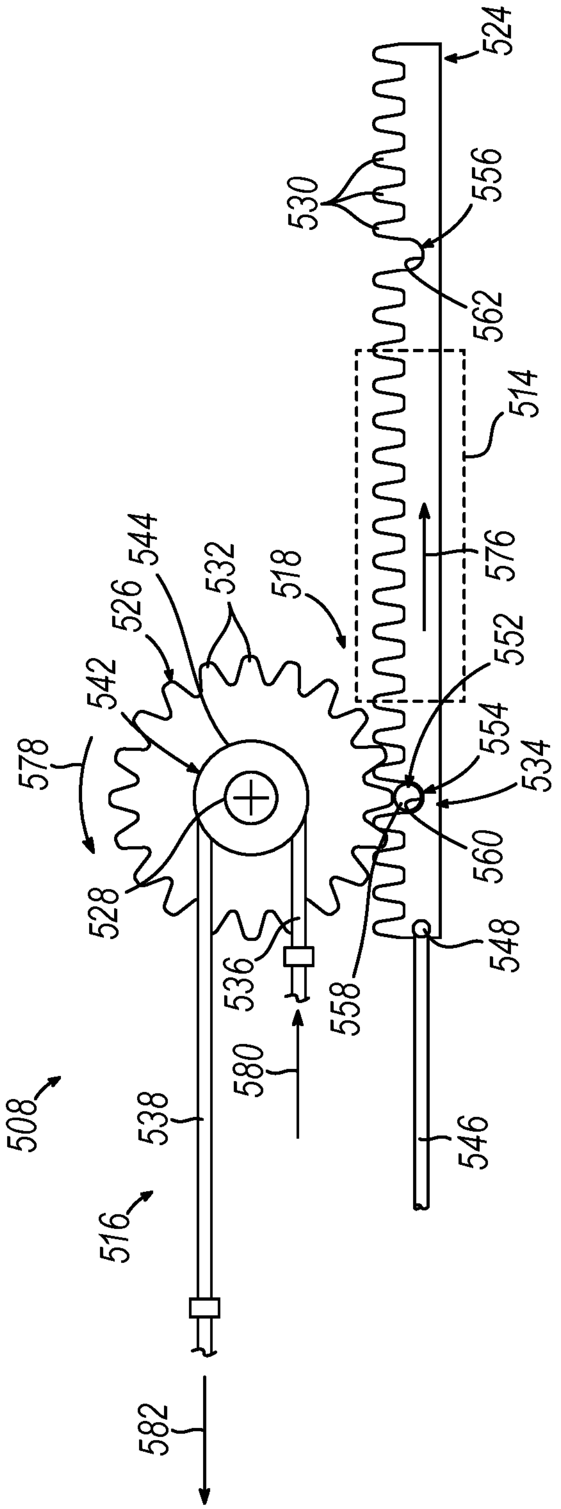
FIG. 15C depicts a top schematic view of the deflection drive assembly of FIG. 15A, but with the linear slider in a third longitudinal position, the rack and pinion assembly in a third longitudinal position, and the locking assembly in a second locked configuration.

FIG. 15C shows a top schematic view of deflection drive assembly (508) of FIG. 15A, but with linear slider (514) in a third longitudinal position, rack and pinion assembly (518) in a third longitudinal position, and locking assembly (534) in a second locked configuration. As shown in FIG. 15C, linear slider (514) is actuated proximally (shown by arrow (576)), which drives rack (524) proximally along longitudinal axis (L-L). The longitudinal motion of rack (524) causes pinion (526) to rotate in a counterclockwise direction (shown by arrow (578)), since teeth (530) of rack (524) are engaged with teeth (532) of pinion (526). The rotation of pinion (526) drives counterclockwise rotation of pulley wheel (542), since pinion (526) and pulley wheel (542) are rotatably coupled. Counter-clockwise rotation of pulley wheel (542) drives counter-clockwise rotation of push-pull cable (160). Particularly, portion (536) of push-pull cable (520) is pulled in a proximal direction (shown by arrow (580)), and portion (538) of push-pull cable (520) is pushed in a distal direction (shown by arrow (582)). As shown in FIG. 15C, in the second locked configuration, cylindraceous pin (558) of locking feature (552) is disposed in cylindraceous detent (560) of locking feature (554). As shown in FIG. 15C, the second locked configuration is the proximal most position of rack (524).

Figure 16C:
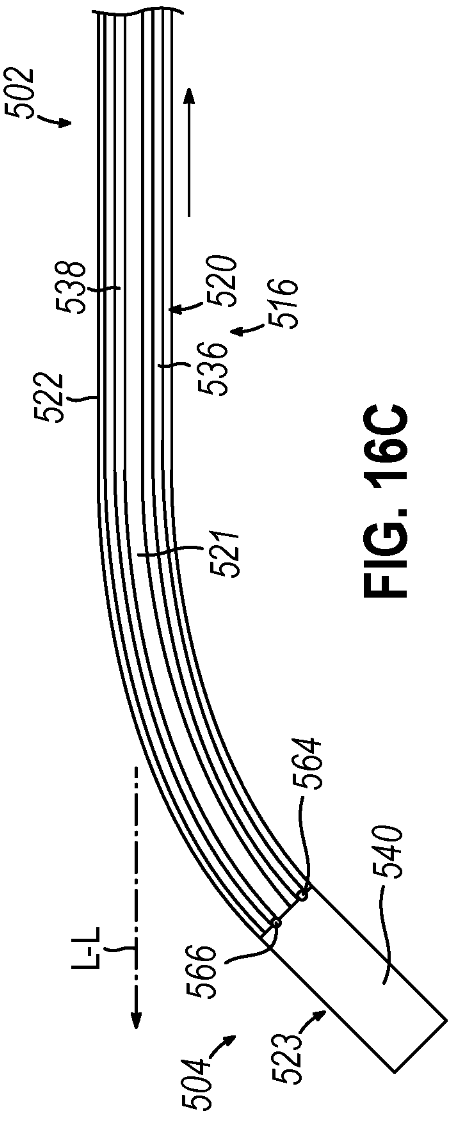
FIG. 16C depicts a top plan view of the distal portion of the catheter of FIG. 13, with a portion of the outer sheath omitted to reveal internal components, where the distal portion of the catheter in a second deflected position associated with the third longitudinal position of the linear slider of FIG. 15C.

FIG. 16C shows a top plan view of distal portion of catheter (502) of FIG. 13, with a portion of outer sheath omitted to reveal internal components, where distal portion of catheter (502) is in a second deflected position associated with third longitudinal position of linear slider (514) of FIG. 15C. Since end effector (504) is shown in the second deflected position, attachment point (564) is disposed proximal to attachment point (566) along longitudinal axis (L-L).

E. Fourth Exemplary Locking Assembly

Figure 17:
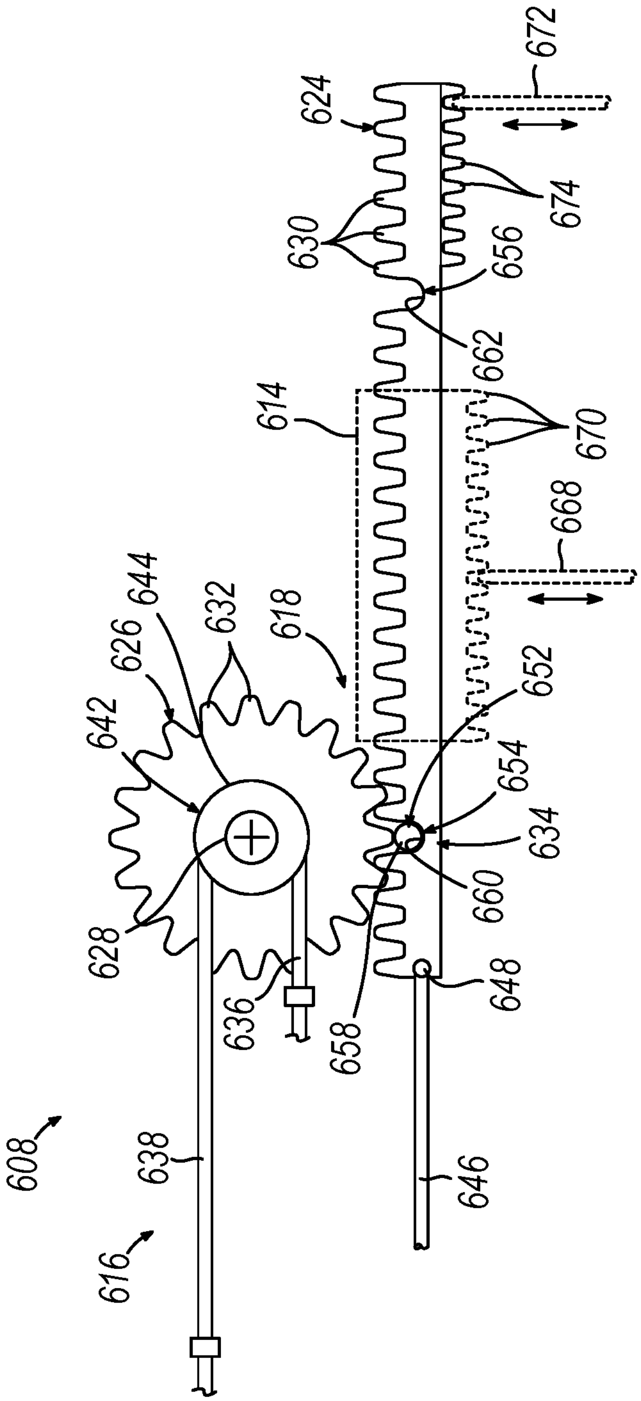
FIG. 17 depicts a top schematic view of a fourth exemplary deflection drive, with a fourth exemplary locking assembly in a locked configuration.

FIG. 17 shows a top schematic view of a fourth exemplary deflection drive assembly (608), with a fourth exemplary locking assembly (634) in a locked configuration. Deflection drive assembly (608) includes a linear slider (614) similar to linear slider (514), a translating assembly (616) similar to translating assembly (516), and a rack and pinion assembly (618) similar to rack and pinion assembly (518). Rack and pinion assembly (618) includes a rack (624) with teeth (630) and a pinion (626) with teeth (632). Rack (624) is coupled with linear slider (614). Locking assembly (634) includes a locking feature (652) on pinion (626) and locking features (654, 656) on rack (624). For example, locking feature (652) is shown as a cylindraceous pin (658), and locking features (654, 656) are cylindraceous detents (660, 662) formed in gear tooth troughs respectively. Cylindraceous pin (658) may be formed together with a pulley wheel (642).

Linear slider (614) is configured to translate along longitudinal axis (L-L) relative to handle (606). Linear slider (614) is coupled with pinion (626) using a shaft (628). Shaft (628) rotatably couples pinion (626) and pulley wheel (642). Deflection drive assembly (608) includes pulley wheel (642) that is co-axial with pinion (626) of rack and pinion assembly (618). Pulley wheel (642) is rotatably coupled with pinion (626) using shaft (628). Pulley wheel (642) includes an interface surface (644) configured to contact push-pull cable (620). A distal portion of rack (524) may be coupled with a wire (546) at an attachment point (548). Push-pull cable (620) has portions (636, 638) similar to push-pull cable (520). Portion (636) of push-pull cable (620) is coupled at an attachment point, similar to attachment point (564) with distal tip member (523) of end effector (504). Portion (638) of push-pull cable (620) is coupled at an attachment point, similar to attachment point (566) with distal tip member (523) of end effector (504).

In lieu of or in addition to locking features (652, 654, 656), locking assembly (634) may include a locking feature (shown as a latching pin (668)), which selectively couples with teeth (670) of linear slider (614) to maintain the deflected angle of end effector (504) (see FIGS. 16A-16C). Latching pin (668) selectively maintains linear slider (614) in the locked position. In lieu of or in addition to locking features (652, 654, 656) or latching pin (668), locking assembly (634) may include a locking feature (shown as a latching pin (672)), which selectively couples with teeth (674) of rack (624) to maintain the deflected angle of end effector (504) (see FIGS. 16A-16C).

F. Exemplary Method

Figure 18:
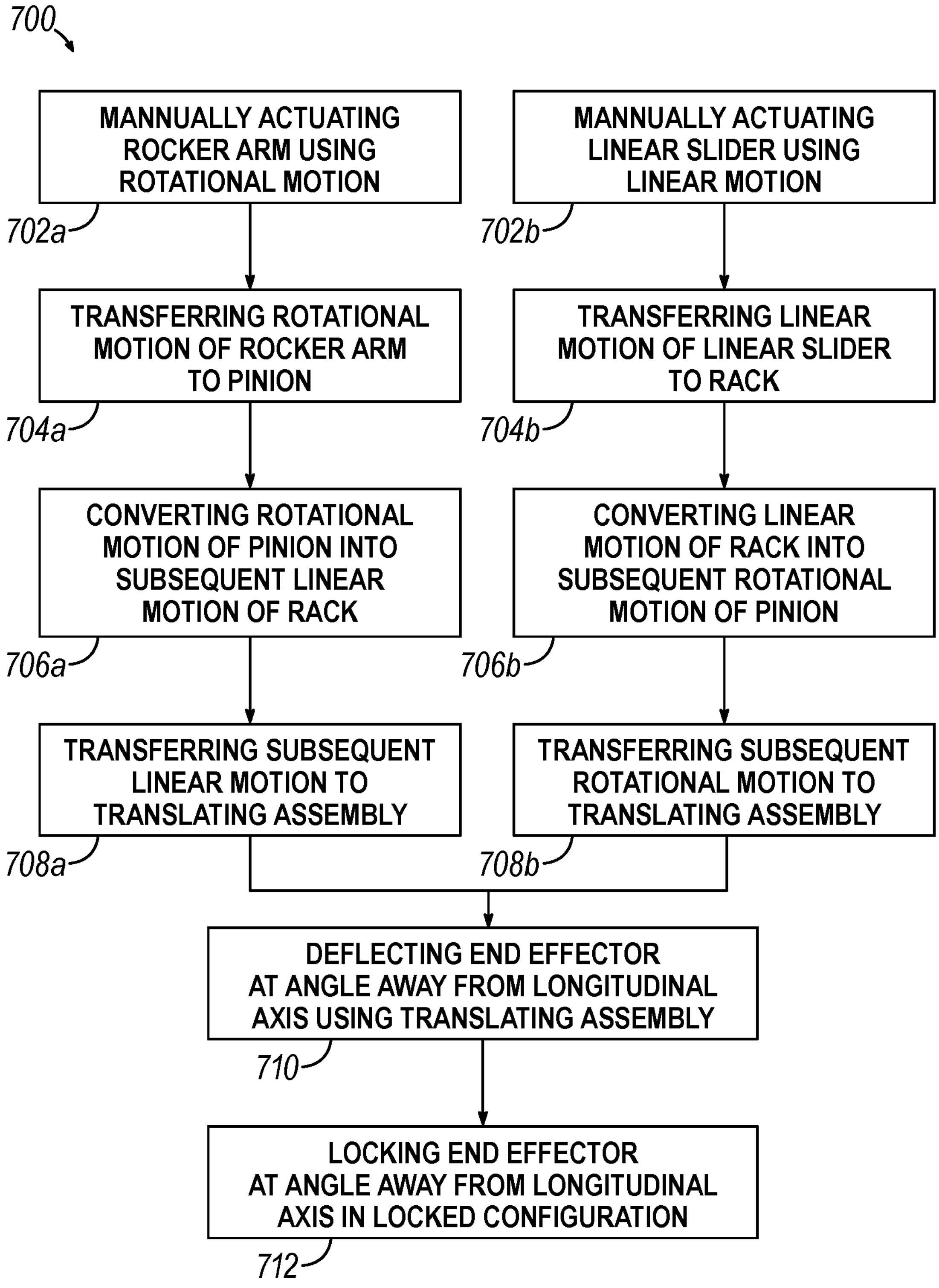
FIG. 18 depicts a diagrammatic view of an exemplary method of operating the catheter assembly of FIG. 1.

FIG. 18 shows a method (700) of operating a catheter assembly (100, 500). Step (702*a*) of method (700) includes manually actuating rocker arm (230, 401) using rotational motion. Step (702*b*) of method (700) includes manually actuating linear slider (514, 614) using linear motion. Step (704*a*) of method (700) includes transferring rotational motion of rocker arm (230, 401) to pinion (308, 408). Step (704*b*) of method (700) includes transferring linear motion of linear slider (514, 614) to rack (524, 624).

Step (706*a*) of method (700) includes converting rotational motion of pinion (308, 408) into subsequent rotational motion of rack (306, 406) using rack and pinion assembly (304, 404). Step (706*b*) of method (700) includes transferring linear motion of rack (524, 624) into subsequent rotational motion of pinion (526, 626) using rack and pinion assembly (518, 618). Step (708*a*) of method (700) includes transferring subsequent linear motion of rack (306, 406) to translating assembly (302, 402). Step (708*b*) of method (700) includes transferring subsequent rotational motion of pinion (526, 626) to translating assembly (516, 616).

Step (710) of method (700) includes deflecting end effector (140) away at an angle relative to longitudinal axis (L-L) using translating assembly (302, 402) or deflecting end effector (504) away at an angle relative to longitudinal axis (L-L) using translating assembly (516, 616). Step (712) of method (700) includes locking end effector (140, 504, 604) at the desired angle away from longitudinal axis (L-L) in the locked configuration using locking assembly (316, 416, 534, 634).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a handle; (b) a catheter extending distally from the handle, a proximal portion of the catheter defining a longitudinal axis; (c) an end effector extending distally from the catheter, the end effector including at least one electrode; and (d) a deflection drive assembly configured to deflect the end effector away from the longitudinal axis, the deflection drive assembly comprising: (i) an input member associated with the handle, (ii) a translating assembly coupled to the end effector, and (iii) a rack and pinion assembly coupled with the input member and the translating assembly, the rack and pinion assembly being configured to drive the translating assembly to deflect the end effector away at an angle relative to the longitudinal axis, the rack and pinion assembly consisting of a rack and a pinion, the rack and pinion assembly being configured to either: (1) transfer rotational motion of the pinion from the input member into linear motion of the rack to push distally or pull proximally the translating member, or (2) transfer linear motion of the rack from the input member into rotational motion of the pinion to move a first end of the translating member proximally and a second end of the translating member distally.

Example 2

The apparatus of Example 1, the input member comprising a rocker arm configured to rotate relative to the handle about a drive axis, the rack and pinion assembly configured to transfer the rotational motion of the pinion from the rocker arm into the linear motion of the rack to push distally or pull proximally the translating member.

Example 3

The apparatus of Example 2, the translating assembly further comprising a push-pull cable coupled with the rack, the deflection drive assembly configured to transfer the linear motion of the rack to either push the push-pull cable in a distal direction or pull the push-pull cable in a proximal direction.

Example 4

The apparatus of any one or more of Examples 2 through 3, the rocker arm and the pinion being co-axial about the drive axis.

Example 5

The apparatus of Example 1, the input member comprising a linear slider configured to move longitudinally along the longitudinal axis, the rack and pinion assembly being configured to transfer the linear motion of the rack from the linear slider into the rotational motion of the pinion to move the first end of the translating member proximally and the second end of the translating member distally.

Example 6

The apparatus of Example 1, the translating assembly further comprising a push-pull cable having first and second portions, the deflection drive assembly being configured to transfer the rotational motion of the pinion to push the first portion of the push-pull cable in a distal direction and pull the second portion of the push-pull cable in a proximal direction.

Example 7

The apparatus of Example 6, the deflection drive assembly further comprising a pulley wheel that is co-axial with the pinion of the rack and pinion assembly, the pulley wheel including an interface surface configured to contact the push-pull cable.

Example 8

The apparatus of any one or more of Examples 5 through 7, the linear slider being fixably coupled with the rack and the pulley wheel being rotatably coupled with the pinion.

Example 9

The apparatus of any preceding Example, further comprising a locking assembly interposed between the input member and the translating assembly, the locking assembly being movable between locked and unlocked configurations, the locking assembly configured to lock the end effector at the angle relative to the longitudinal axis in the locked configuration.

Example 10

The apparatus of Example 9, the locking assembly comprising first and second locking features configured to transition between a locked configuration and an unlocked configuration, the locking assembly being configured to prevent the translating assembly from translating along the longitudinal axis in the locked configuration.

Example 11

The apparatus of Example 10, the first locking feature being disposed on the pinion, the second locking feature being disposed on the rack, the second locking feature being complementary to the first locking feature, the first and second locking features being configured to engage one another in the locked configuration, the first and second locking features being configured to be spaced at a distance from one another in the unlocked configuration.

Example 12

The apparatus of any one or more of Examples 10 through 11, the first and second locking features being cylindraceous.

Example 13

The apparatus of Example 12, the first locking feature including a cylindraceous pin, the second locking feature including a cylindraceous detent configured to receive the cylindraceous pin in the locked configuration.

Example 14

The apparatus of Example 13, the cylindraceous pin projects unitarily from the input member, the cylindraceous detent being formed into a gear tooth trough of the rack.

Example 15

The apparatus of any of Examples 9 through 14, the locking assembly further comprising a biasing member configured to bias the rack away from the pinion to switch to the unlocked configuration.

Example 16

The apparatus of any one or more of Examples 1 through 8, further comprising a locking assembly, the locking assembly comprising first and second locking features configured to transition between a locked configuration and an unlocked configuration, the first locking feature being disposed on the translating assembly and the second locking feature being selectively positioned on the handle.

Example 17

The apparatus of Example 10, the input member comprising a rocker arm configured to rotate relative to the handle about a drive axis, the first locking feature being disposed on the rocker arm and the second locking feature being movable on the handle.

Example 18

The apparatus of Example 17, the drive axis being perpendicular with the longitudinal axis.

Example 19

The apparatus of Example 10, the input member comprising a linear slider configured to translate relative to the handle along the longitudinal axis, the first locking feature being disposed on the linear slider and the second locking feature being movable on the handle.

Example 20

The apparatus of Example 1, the translating assembly consisting of a single push-pull cable, the rack and pinion assembly being configured to drive the single push-pull cable in opposing directions.

Example 21

The apparatus of Example 20, the single push-pull cable comprising a stainless-steel rod.

Example 22

The apparatus of any one or more of Examples 1 through 21, the at least one electrode being configured to emit RF energy.

Example 23

The apparatus of any one or more of Examples 1 through 22, the at least one electrode being configured to perform electrophysiology mapping.

Example 24

The apparatus of any one or more of Examples 1 through 23, the end effector comprising a strain gauge assembly.

Example 25

The apparatus of any one or more of Examples 1 through 24, the end effector being configured to emit irrigation fluid.

Example 26

The apparatus of any one or more of Examples 1 through 25, the end effector comprising a position sensor.

Example 27

An apparatus, comprising: (a) a handle; (b) a catheter extending distally from the handle, a proximal portion of the catheter defining a longitudinal axis; (c) an end effector extending distally from the catheter, the end effector including at least one electrode; (d) a deflection drive assembly configured to deflect the end effector away from the longitudinal axis, the deflection drive assembly comprising: (i) an input member associated with the handle, (ii) a translating assembly coupled to the end effector, the input member being configured to drive the translating assembly to deflect the end effector away at an angle from the longitudinal axis, and (iii) a rack and pinion assembly coupled with the input member and the translating assembly, the rack and pinion assembly consisting of a rack and a pinion, the rack and pinion assembly configured to either: (1) transfer rotational motion of the pinion from the input member into linear motion of the rack to push distally or pull proximally the translating member, or (2) transfer linear motion of the rack from the input member into rotational motion of the pinion to move a first end of the translating member proximally and a second end of the translating member distally; and (e) a locking assembly configured to transition between a locked configuration and an unlocked configuration, the locking assembly comprising first and second locking features, the first and second locking features configured to lock the end effector at the angle away from the longitudinal axis in the locked configuration, the first and second locking features configured to allow the end effector to move along a range of angles in the unlocked configuration.

Example 28

The apparatus of Example 27, the locking assembly being interposed between the input member and the translating assembly, the locking assembly being configured to prevent the translating assembly from translating along the longitudinal axis in the locked configuration.

Example 29

The apparatus of Example 28, the first locking feature being disposed on the pinion, the second locking feature being disposed on the rack, the second locking feature being complementary to the first locking feature, the first and second locking features are configured to engage one another in the locked configuration, the first and second locking features are configured to be spaced at a distance from one another in the unlocked configuration.

Example 30

The apparatus of claim of any one or more of Examples 27 through 30, the first and second locking features being cylindraceous.

Example 31

The apparatus of Example 30, the first locking feature being a cylindraceous pin, the second locking feature being a cylindraceous detent configured to receive the cylindraceous pin in the locked configuration.

Example 32

A method of operating an apparatus, the apparatus comprising: (a) a handle; (b) a catheter extending distally from the handle, a proximal portion of the catheter defining a longitudinal axis; (c) an end effector extending distally from the catheter, the end effector including at least one electrode; and (d) a deflection drive assembly configured to deflect the end effector away from the longitudinal axis, the deflection drive assembly comprising: (i) an input member associated with the handle, (ii) a translating assembly coupled to the end effector, and (iii) a rack and pinion assembly coupled with the input member and the translating assembly, the rack and pinion assembly consisting of a rack and a pinion, the method comprising: (a) manually actuating the input member using rotational motion or linear motion; (b) transferring the rotational motion of the input member to the pinion or transferring the linear motion of the input member to the rack; (c) transferring the rotational motion of the pinion into subsequent linear motion of the rack or transferring the linear motion of the rack into subsequent rotational motion of the pinion using the rack and pinion assembly; (d) transferring the subsequent linear motion to the translating assembly or the subsequent rotational motion to the translating assembly; and (e) deflecting the end effector at an angle away from the longitudinal axis using the translating assembly.

Example 33

The method of Example 32, further comprising locking the end effector at the angle away from the longitudinal axis in the locked configuration.

Example 34

A method of manufacturing an apparatus, the apparatus comprising: (a) a handle; (b) a catheter extending distally from the handle, a proximal portion of the catheter defining a longitudinal axis; (c) an end effector extending distally from the catheter, the end effector including at least one electrode; and (d) a deflection drive assembly configured to deflect the end effector away from the longitudinal axis, the deflection drive assembly comprising: (i) an input member associated with the handle, (ii) a translating assembly coupled to the end effector, and (iii) a rack and pinion assembly coupled with the input member and the translating assembly, the rack and pinion assembly consisting of a rack and a pinion, the method comprising: (a) inserting the pinion to be engaged with the rack at a first position configured for uni-directional end effector deflection that is longitudinally spaced from than a second position along the rack for bi-directional end effector deflection or inserting the pinion to be engaged with the rack at a third position configured for bi-directional end effector deflection that is longitudinally spaced from a fourth position along the rack for uni-directional end effector deflection; and (b) attaching the translating assembly with the rack and pinion assembly.

V. MISCELLANEOUS

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a handle;

(b) a catheter extending distally from the handle, a proximal portion of the catheter defining a longitudinal axis;

(c) an end effector extending distally from the catheter, the end effector including at least one electrode;

(d) a deflection drive assembly comprising:

(i) an input member associated with the handle, (ii) a translating assembly coupled to the end effector, and (iii) a rack and pinion assembly comprising a pinion responsive to the input member with rotational motion and a rack with linear motion transferred from the rotational motion of the pinion to translational motion of the translating assembly to push distally or pull proximally the translating assembly in deflecting the end effector, the pinion having a first plurality of teeth and the rack having a second plurality of teeth, the first and second pluralities of teeth configured to cooperate to thereby transfer the rotational motion of the pinion to the translational motion of the translating assembly, the translating assembly comprising a push-pull cable with a proximal end coupled to the rack and a distal end coupled to the end effector; and (e) a locking assembly interposed between the input member and the translating assembly, the locking assembly comprising a pin disposed on at least one of the first plurality of teeth of the pinion and a detent configured in the rack between proximal teeth and distal teeth of the second plurality of teeth of the rack, the pin configured to engage the detent to releasably lock the end effector in deflection at a selected angle relative to the longitudinal axis.

2. The apparatus of claim 1, the input member comprising a rocker arm configured to rotate relative to the handle about a drive axis, the rack and pinion assembly configured to transfer the rotational motion of the pinion from the rocker arm into the linear motion of the rack to push distally or pull proximally the translating assembly.

3. The apparatus of claim 2, the rocker arm and the pinion being co-axial about the drive axis.

4. The apparatus of claim 2, wherein the pin projects from the rocker arm.

5. The apparatus of claim 1, wherein the locking assembly is movable between locked and unlocked configurations, the locking assembly configured to lock the end effector at the selected angle relative to the longitudinal axis in the locked configuration.

6. The apparatus of claim 5, wherein the locking assembly is configured to prevent the translating assembly from translating along the longitudinal axis in the locked configuration.

7. The apparatus of claim 6, the pin and the detent being configured to engage one another in the locked configuration, the pin and the detent being configured to be spaced at a distance from one another in the unlocked configuration.

8. The apparatus of claim 5, the locking assembly further comprising a biasing member configured to bias the rack away from the pinion to disengage the pin from the detent.

9. The apparatus of claim 8, wherein the rack is constructed of a bendable material.

10. The apparatus of claim 8, wherein the handle is configured to actuate the biasing member.

11. The apparatus of claim 1, the translating assembly consisting of a single push-pull cable, the rack and pinion assembly being configured to drive the single push-pull cable in opposing directions.

12. The apparatus of claim 1, the at least one electrode being configured to emit RF energy.

13. The apparatus of claim 1, the at least one electrode being configured to perform electrophysiology mapping.

14. The apparatus of claim 1, wherein the pin upon rotational movement from the input member is configured to move into the detent on the rack, wherein the pinion is free to rotate when the pin is outside of the detent and the pinion is locked against rotation when the pin is received in the detent.

15. The apparatus of claim 1, wherein the locking assembly further comprises a second detent at a second location on the rack different from a first location of the detent.

16. The apparatus of claim 15, wherein engagement of the pin in the detent at the first location locks the end effector in a neutral configuration aligned with the longitudinal axis, and engagement of the pin in the second detent in the second location locks the end effector in a deflection configuration at the selected angle relative to the longitudinal axis.

17. The apparatus of claim 1, wherein the pinion is configured for bidirectional rotation in a first direction that moves the rack in a distal direction and a second direction that moves the rack in a proximal direction.

18. The apparatus of claim 1, wherein the pin is positioned adjacent to a gear tooth tip of the pinion.

19. The apparatus of claim 1, wherein the detent is formed in a gear tooth trough of the rack.

20. The apparatus of claim 1, wherein the detent is configured as a deeper gear tooth trough in the rack.

* * * * *